(12) United States Patent
Wu et al.

(10) Patent No.: US 7,834,216 B2
(45) Date of Patent: Nov. 16, 2010

(54) DESMOSDUMOTINS, THE METHOD FOR PREPARING THE SAME AND USE AS ANTI-TUMOR OR ANTI-AIDS AGENTS

(75) Inventors: Jiuhong Wu, Suite 602, Unit 6, Building No. 5, Jingshi Yuan, Lin-Cui Road, Chaoyang District, Beijing 100085 (CN); Kyoko Nakagawa-Goto, Chapel Hill, NC (US); Xihong Wang, Beijing (CN); Ning Shi, Beijing (CN)

(73) Assignee: Jiuhong Wu, Beijing (CN)

( * ) Notice: Subject to any disclaimer, the term of this patent is extended or adjusted under 35 U.S.C. 154(b) by 310 days.

(21) Appl. No.: 11/794,422

(22) PCT Filed: Dec. 28, 2005

(86) PCT No.: PCT/CN2005/002334
§ 371 (c)(1),
(2), (4) Date: Aug. 6, 2008

(87) PCT Pub. No.: WO2006/069533
PCT Pub. Date: Jul. 6, 2006

(65) Prior Publication Data
US 2009/0233998 A1  Sep. 17, 2009

(30) Foreign Application Priority Data
Dec. 29, 2004  (CN) .................. 2004 1 0103642

(51) Int. Cl.
*C07C 49/303* (2006.01)
*C07D 311/00* (2006.01)
*A61K 31/12* (2006.01)
*A61K 31/25* (2006.01)

(52) U.S. Cl. .................. 568/337; 549/403; 514/456; 514/688

(58) Field of Classification Search .............. 568/337; 549/403
See application file for complete search history.

(56) References Cited

U.S. PATENT DOCUMENTS 5,411,728 A * 5/1995 Joulain et al. .............. 424/59

FOREIGN PATENT DOCUMENTS

| CN | 1098903 | 2/1995 |
|---|---|---|
| CN | 1126471 | 7/1996 |
| CN | 1335292 | 2/2002 |
| CN | 1611497 | 5/2005 |
| WO | WO 02/089587 | 11/2002 |

OTHER PUBLICATIONS

Wu et al. Anti-AIDS Agents 54. A Potent Anti-HIV Chalcone and Flavanoids from Genus Desmos. Biorganic & Medicinal Chemistry Letters, 2003,vol. 13, p. 1813-1815.*
Wu et al. Desmosdumotin C, a novel cytotoxic principle from *Desmos dumosus*. Tetrahedron Letters 43, 2002, p. 1391-1393.*
Nishizawa, et al. "Structure of Syzygiol: A Skin-Tumor Promotion Inhibitor", Tetrahedron Letters (1991), 32(2), pp. 211-212.
Sbit, et al., "Structure of Ceroptene", Acta Crystallographica, Section C: Crystal Structure Communications, (1987), C43(11), pp. 2204-2206.
Vilain, et al., "α-Diceroptene: A New Dimeric Structure for Isoceroptene", Zeitschrift Fuer Naturforschung, C: Journal of Biosciences (1987), 42(7-8), pp. 849-854.
Markham, et al., "Isoceroptene, A Novel Polyphenol from Pityrogramma Triangularis", Zeitschrift Fuer Naturforschung, C. Journal of Biosciences (1985), 40C(5-6), pp. 317-320.
Dreyer, et al., "Extractives of Dalea Species (Leguminosae)", Tetrahedron (1975), 31(4), pp. 287-293.
Bick, et al., "Nuclear Magnetic Resonance Studies. V. The Tautomerism of Tasmanone and related β-Triketones", Australian Journal of Chemistry (1965), 18(9), pp. 1405-1410.
Forsen, "Molecular Orbital Calculations of Some Enolized Di- and Triketones. II. Charge Distributions and Bond Orders. Comparison with Infrared and Proton Magnetic Resonance Data", Arkiv. Kemi (1962), 20, pp. 25-40.
Forsen, et al., "Proton Magnetic Resonance Studies of Enolized β-Triketones", Acta Chemica Scandinavica (1959), 13, pp. 1383-1394.
Sato, et al., "Synthesis of Model Compounds of Safflomin C", Bulletin of the Chemical Society of Japan (1992), 65(2), pp. 452-457.
Sato, et al., "Synthesis of Syzygiol; A Skin-Tumor Promotion Inhibitor", Bulletin of the Chemical Society of Japan (1992), 65(9), pp. 2552-2554.
Sato, et al., "Efficient Synthesis of Analogs of Safflower Yellow B, Carthamin, and its Precursor: Two Yellow and One Red Dimeric Pigments in Safflower Petals", Tetrahedron (2005), 61(40), pp. 9630-9636.
Nakagawa-Goto, et al., "First Total Synthesis of Desmosdumotin C", Synthetic Communications (2005), 35(13), pp. 1735-1739.
Nakagawa-Goto, et al., "Antitumor Agents 243. Syntheses and Cytotoxicity of Desmosdumotin C Derivatives", Bioorganic & Medicinal Chemistry (2005), 13(6), pp. 2325-2330.
International Search Report for International Application No. PCT/CN2005/002334 mailed Mar. 2, 2006.

* cited by examiner

*Primary Examiner*—Sikarl A Witherspoon
(74) *Attorney, Agent, or Firm*—Pearl, Cohen Zedek Latzer, LLP

(57) ABSTRACT

This invention discloses the method for preparing desmosdumotin C, the series of desmosdumotin C derivatives and their manufactures, and the total synthesis of desmosdumotin B. The invention also discloses uses of the derivatives and pharmaceutical compositions containing the same in preparation of medicines for treatment of tumor or AIDS.

20 Claims, No Drawings

DESMOSDUMOTINS, THE METHOD FOR PREPARING THE SAME AND USE AS ANTI-TUMOR OR ANTI-AIDS AGENTS

CROSS-REFERENCE TO RELATED APPLICATIONS

This application is a National Phase Application of PCT International Application No. PCT/CN2005/002334, entitled "DESMOSDUMOTINS, THE METHOD FOR PREPARING THE SAME AND USE AS ANTI-TUMOR OR ANTI-AIDS AGENTS", International Filing Date Dec. 28, 2005, published on Jul. 6, 2006 as International Publication No. WO 2006/069533, which in turn claims priority from Chinese Patent Application No. 200410103642.0, filed Dec. 29, 2004, both of which are incorporated herein by reference in their entirety.

FIELD OF THE INVENTION

The invention relates to the total synthesis method of the novel desmosdumotin C and its derivatives; the series of desmosdumotin C derivatives as leading compound and their manufactures; and the synthesis of Domosdumotin B; the applications of the above chemical structures and medicinal compositions containing them in manufacturing medicines for treating tumor, AIDS and virus.

BACKGROUND OF THE INVENTION

Desmosdumotin C was extracted, isolated and purified as a novel anti-tumor compound from the root of *Desmos dumosus*, which has been used in Chinese folk medicine. The unique structure has been awarded Chinese patent No. ZL01126471.3.

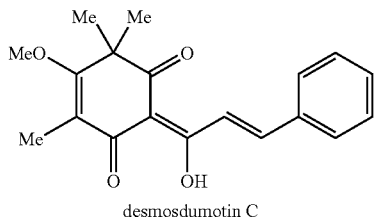

desmosdumotin C

2-[(1'-hydroxy-2'-ene-3'-phenyl)propenylene]-5-methoxy-4,6,6-trimethyl-1,3-cyclohexene(4,5)-dione Based on the anti-cancer activity in vitro testing, Desmosdumotin C showed significant inhibition to several kinds of tumor cells, with the inhibiting strength of HOS (bone cancer cell): $ED_{50} < 2.5$ μg/ml, MCF-7 (breast cancer cell): $ED_{50} < 3.8$ μg/ml. IA9 (ovarian cancer cell) is $ED_{50} < 4.0$ μg/ml. In addition, it was more active against vincristine-resistant KB cells ($ED_{50} < 5.6$ μg/ml) than against the parent KB epidermoid nasopharyngeal carcinoma cell line ($ED_{50} < 6.5$ μg/ml).

SUMMARY OF THE INVENTION

The aim of the invention is to treat Desmosdumotin C as leading compound, synthesis method, synthesis of new derivates of Desmosdumotin C, and develops a series of novel anti-tumor or anti HIV compound for high anti-tumor or anti-AIDS with the activated groups by the researching of its structures and activity.

In order to achieve the aim, in the first aspect, the present invention provides the compound of the following formula (I),

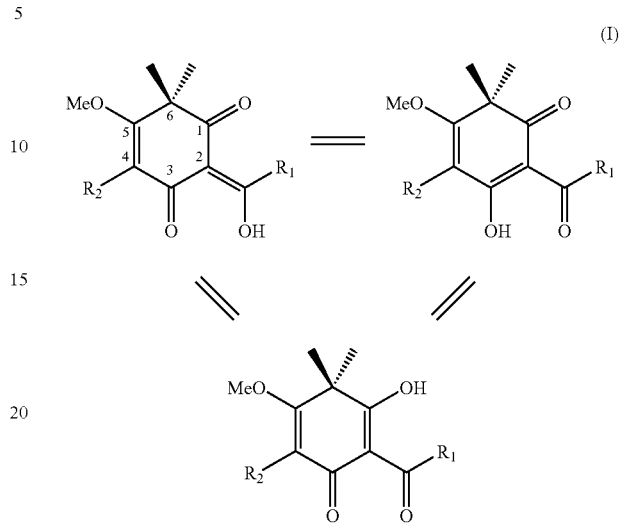

Wherein $R_1=C_2-C_8R_1'$, $R_2$ is hydrogen lower saturated or unsaturated alkyl, halogen, hydroxyl, alkoxy, aryl, substituted aryl, substituted heterocycle.

Wherein C2-C8 is saturated or unsaturated alkyl.

Wherein $R_1'$ is selected from the groups consisting of aromatic ring; substituted aromatic ring with the group selecting from halogen, hydroxyl, lower alkyl, alkoxy, furyl, thienyl, and thiazoly, unsaturated aromatic heterocyclic ring; and substituted aromatic heterocyclic ring with the group selecting from halogen, hydroxyl, lower alkyl, alkoxy, furyl, thienyl, and thiazoly.

wherein $R_1$ is preferably —$CH_2$=$CH_2R_1'$, wherein $R_1'$ is selected from the groups consisting of aromatic ring; substituted aromatic ring with the group selecting from halogen, hydroxyl, lower alkyl, alkoxy, furyl, thienyl, and thiazoly; unsaturated aromatic heterocyclic ring; and substituted aromatic heterocyclic ring with the group selecting from halogen, hydroxyl, lower alkyl, alkoxyl, furyl, thienyl, and thiazoly, more preferably, $R_1'$ is selected from the group consisting of 4-bromophenyl, 4-chlorophenyl, 4-iodophenyl, hydroxyl substituted phenyl, lower alkyl substituted phenyl, alkoxy substituted phenyl, 2-furyl, 2-thiophene, and 2-thiazoly.

In particular, the compounds of the invention comprise:
2-[1'-Hydroxy-3-(4-bromophenyl)-allylidene]-5-methoxy-4,6,6-trimethylcyclohex-4-ene-1,3-dione;
2-[1'-Hydroxy-3-(2-methoxyphenyl)-allylidene]-5-methoxy-4,6,6-trimethylcyclohex-4-ene-1,3-dione;
2-[1'-Hydroxy-3-(3-methoxyphenyl)-allylidene]-5-methoxy-4,6,6-trimethyl-cyclohex-4-ene-1,3-dione
2-[1'-Hydroxy-3-(4-methoxyphenyl)-allylidene]-5-methoxy-4,6,6-trimethyl-cyclohex-4-ene-1,3-dione
2-[1'-Hydroxy-3-(4-hydroxyphenyl)-allylidene]-5-methoxy-4,6,6-trimethyl-cyclohexen-4-ene-1,3-dione
2-(3'-Furan-2"-yl-1'-hydroxy-allylidene)-5-methoxy-4,6,6-trimethyl-cyclohex-4-ene-1,3-dione
2-(1'-Hydroxy-3'-thiophen-2"-yl-allylidene)-5-methoxy-4,6,6-trimethyl-cyclohex-4-ene-1,3-dione
2-[(1'-Hydroxy-3'-thiazol-2-yl-allylidene)-5-methoxy-4,6,6-trimethyl-1,3-cyclohex-4-ene-1,3-dione
2-[(1'-hydroxy-2'-ene-3'-phenyl)propenylene]-5-hydroxy-4,6,6-trimethyl-1,3-cyclohexene(4,5)-dione.

2-[(1'-hydroxy-2'-ene-3'-phenyl)propenylene]-5-methoxy-4,6,6-trimethyl-1,3-cyclohexene(4,5)-dione.

In the second aspect the present invention provides a method for preparing the compound of formula (I), said method comprising the steps of:
a) Dissolving 2,4,6,-trihydroxyacctophenone and sodium methoxide in absolute alcohol, refluxing the 2,4,6,-trihydroxyacctophenone and sodium methoxide in the presence of methyl iodide to obtain a mixture; cooling and acidifying the mixture with HCL, then extracting the mixture with EtOAc to obtain organic layers; combining the organic layers, following by drying and concentrating the organic layers to produce 2-Acetyl-4,6,6-trimethylcyclonhexa-1,3,5-trione;
b) Selectively methoxylating 2-Acetyl-4,6,6-trimethylcyclonhexa-1,3,5-trione to obtain 2-Acetyl-5-methoxy-4,6,6-trimethylcyclonhexa-1,3-dione with −78° C. of the reaction temperature;
c) Stirring a solution of 2-Acetyl-5-methoxy-4,6,6-trimethylcyclohexa-1,3-dione in EtOH and 50% KOH in water and benzaldehyde at room temperature to obtain a mixture; extracting the mixture, washing the mixture with water, following by drying, concentrating, isolating and recrystallizing the mixture to obtain 2-[(1'-hydroxy-2'-ene-3'-phenyl)propenylene]-5-methoxy-4,6,6-trimethyl-1,3-cyclohexene(4,5)-dione.

The above method fierier comprises the step of substituting Benzaldehyde in the step C by using the following groups: 4-bromophenylaldehyde, o-, p-, and m-anisaledhyde, 2-furaldehyde, 2-thiophenecarboxaldehyde, and 2-thiazolecarboxaldehyde.

In the third aspect, the present invention provides a method for preparing the compounds of formula (I), said method comprising the steps of:
a) Stiffing 2,4,6,-trihydroxyacctophenone in AcOH, and refluxing the 2,4,6,-trihydroxyacctophenone in AcOH in presence of $Ac_2O$ and $BF_3OEt_2$ to obtain a mixture; cooling and adjusting the mixture to pH2-6 by NaOH, extracting the mixture by 5% MeOH/AcOEt to obtain organic layers, combining the organic layers, following by drying in vacuum to obtain a product; dissolving the product in the MeOH and refluxing the product in MeOH in presence of NaOH at room temperature to obtained a refluxed product; acidifying the refluxed product with HCL, then extracted the refluxed product with MeOH/AcOEt to obtain an extract, washing the extract, following by drying and purifying by silica gel column to obtain 1,5-Diacetyl-2,4,6-trihydroxybenzene;
b) Conducting a strong redox of 1,5-Diacetyl-2,4,6-trihydroxybenzene with concentrated $H_2SO_4$ to obtain a mixture, methoxylated the mixture with $TMSCHN_2$, then extracting the mixture with MeOH/AcOEt to obtain 2-acetyl-5-methoxy-6,6-dimethylcyclohexane-1,3-dione;
c) Reacting a solution of 2-acetyl-5-methoxy-6,6-dimethylcyclohexane-1,3-dione in EtOH aq KOH with benzaldehyde to obtain a extract; washing, drying, concentrating, isolating and recrystallizing the extract.

In the forth aspect, the present invention relates to the use of the compounds of formula (I) in preparing the pharmaceuticals for the treatment of anti-tumor, anti-AIDS agents, and anti-other virus diseases.

In the fifth aspect, the present invention relates to a pharmaceutical compositions containing the pharmaceutically effective amount of the compound of formula (I) and pharmaceutically acceptable carrier. The present invention also relates to the use of the composition in preparing the pharmaceuticals for the treatment of anti-tumor, anti-AIDS agents, and anti-other virus.

In the sixth aspect, the present invention relates to an intramolecular cyclizated compounds having the formula (II) and (III) produced by the intramolecular cyclization between $R_1$ and position 2-carbonyl in the compound of formula (I).

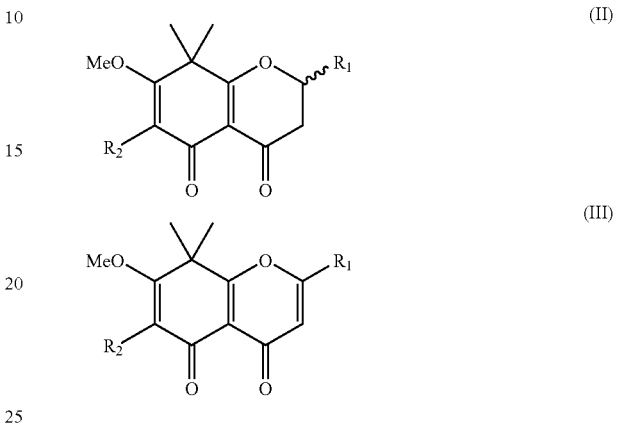

wherein $R_1=C_2-C_8R_1'$, $R_2$ is hydrogen, lower saturated or unsaturated alkyl, halogen, hydroxyl, alkoxyl, aryl, substituted aryl or heterocycle.

wherein $C_2-C_8$ is saturated or unsaturated alkyl that represents cis- and trans-isomer.

wherein $R_1'$ is selected from the groups consisting of aromatic ring; substituted aromatic ring with the group selecting from halogen, hydroxyl, lower alkyl, alkoxyl, furyl, thienyl, and thiazoly; unsaturated aromatic heterocyclic ring; and substituted aromatic heterocyclic ring with the group selecting from halogen, hydroxyl, lower alkyl, alkoxyl, furyl, thienyl, and thiazoly.

Preferably, $R_1$ is $—CH_2=CH_2R_1'$, wherein $R_1'$ is selected from the groups consisting of aromatic ring; substituted aromatic ring with the group selecting from halogen, hydroxyl, lower alkyl, alkoxyl, furyl, thienyl, and thiazoly; unsaturated aromatic heterocyclic ring; and substituted aromatic heterocyclic ring with the group selecting from halogen, hydroxyl, lower alkyl, alkoxyl, furyl, thienyl, and thiazoly. More preferably, $R_1'$ is selected from the group consisting of 4-bromophenyl, 4-chlorophenyl, 4-iodophenyl, hydroxy substituted phenyl, lower alkyl substituted phenyl, alkoxy substituted phenyl, 2-furyl, 2-thiophene, and 2-thiazoly.

In particular, the cyclizated compounds of the invention comprises:
7-hydroxyl-6,8,8-trimethyl-2-phenyl-2,3-dihydrogen-8H-chromene-4,5-dione,
7-hydroxyl-6,8,8-trimethyl-2-phenyl-1-5H-chromene-4,5-dione,
7-methoxy-6,8,8-trimethyl-2-phenyl-8H-chromene-4,5-dione,
7-methoxy-8,8-dimethyl-2-phenyl-8H-naphthene-4,5-dione.

In the seventh aspect, the present invention provides two methods for preparing the cyclizated compound of formula (II) and (III), the first comprises the steps of:
a) Conducting Improved Marchand reaction using 2,4,6-trihydroxyacctophenone as the initial material; dissolving 2,4,6,-trihydroxyacctophenone in AcOH, refluxing the 2,4,6,-trihydroxyacctophenone in AcOH in the presence of $Ac_2O$ and $BF_3OEt_2$; cooling and adjusted the mixture to pH2-6 by NaOH, extracting the mixture by 5% MeOH/ AcOEt to obtain organic layers, combining the organic layers, following by drying and dissolving the organic layers in the MeOH to obtain a product; stirring the product with NaOH at room temperature; acidifying the product with HCL, then extracting the product with MeOH/AcOEt to obtain an extract, washing, drying and purifying the extract by silica gel column to obtain 1,5-diacetyl-2,4,6-trihydroxybenzene;

b) Conducting a strong redox of 1,5-diacetyl-2,4,6-trihydroxybenzene with concentrated $H_2SO_4$ to obtain a mixture, methoxylating the mixture using $TMSCHN_2$, then extracting the mixture with MeOH/AcOEt to obtain 2-acetyl-5-methoxy-6,6-dimethylcyclohexane-1,3-dione;

c) Reacting a solution of 2-acetyl-5-methoxy-6,6-dimethyl-cyclohexane-1,3-dione in EtOH aq KOH with benzaldehyde in the presence of strong base to obtain a mixture; extracting the mixture by dichloromethane, then washing the mixture by water, following by drying, concentrating, isolating and recrystallizing the mixture to obtain 2-[(1'-hydroxy-2'-ene-3'-phenyl)propenylene]-5-methoxy-6,6-dimethyl-1,3-cyclohexene(4,5)-dione;

d) Dissolving 2-[(1'-hydroxy-2'-ene-3'-phenyl)propenylene]-5-methoxy-6,6-dimethyl-1,3-cyclohexene(4,5)-dione in DMSO, and adding 0.5 v/w % $I_2$ and concentrated $H_2SO_4$ to obtain a mixture; heating the mixture; droplet adding the concentrated $H_2SO_4$ to the mixture; following by quenching the mixture in ice-cold bath with 10% $Na_2S_2O_3$; extracting the mixture with EtoAc to obtain an extract, washing the extract by water, following by drying, chromatographing the extract on silica gel to obtain the compound.

The second method comprises the steps of:

a) Dissolving 2,4,6,-trihydroxyacctophenone in absolute alcohol, refluxing 2,4,6,-trihydroxyacctophenone in absolute alcohol with methyl iodide to obtain a mixture; cooling and acidifying the mixture with HCL, then extracting the mixture with EtOAc to obtain organic layers; combining the organic layers, drying and concentrating the organic layers to produce 2-acetyl-4,6,6-trimethylcyclonhexa-1,3,5-trione;

b) Selectively methoxylating 2-acetyl-4,6,6-trimethylcyclonhexa-1,3,5-trione to obtain 2-acetyl-3-hydroxy-5-methoxy-4,6,6-trimethylcyclonhexa-1,3-dione with −78° C. of the reaction temperature;

c) Stirring a solution of 2-acetyl-5-methoxy-4,6,6-trimethylcyclonhexa-1,3-dione in EtOH and 50% KOH in water and benzaldehyde at room temperature to obtain a mixture; extracting the mixture, washing the extract with water, drying, concentrating, isolating and recrystallizing the extract to obtain 2-[(1'-hydroxy-2'-ene-3'-phenyl)propenylene]-5-methoxy-4,6,6-trimethyl-1,3-cyclohexene(4,5)-dione;

d) To a solution of 2-[(1'-hydroxy-2'-ene-3'-phenyl)propenylene]-5-methoxy-4,6,6-trimethyl-1,3-cyclohexene(4,5)-dione in DMSO, $I_2$ and concentrated $H_2SO_4$ was added to obtain a mixture; beating the mixture at 50~90° C., preferably 80° C.; extracting the mixture and then washing, drying, and concentrating the mixture in vacuum.

In the eighth aspect, the present invention relates to the use of compound of formula (II) and/or (III) in preparing the pharmaceuticals for the treatment of anti-tumor, anti-AIDS agents, and anti-other virus diseases.

In the ninth aspect, the present invention relates to a pharmaceutical compositions containing the pharmaceutically effective amount of the compound of formula (II) and/or (III) and pharmaceutically acceptable carrier. The present invention also relates to the use of the composition in preparing the pharmaceuticals for the treatment of anti-tumor, anti-AIDS agents, and anti-other virus.

In the tenth aspect, the present invention relates to a method for preparing Desmosdumotin C having the following structure, comprising the steps of:

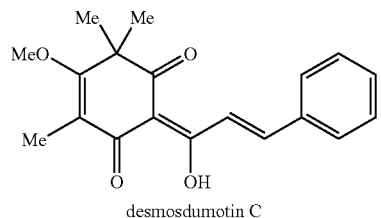

desmosdumotin C a) Dissolving 2,4,6,-trihydroxyacctophenone and sodium methoxide in absolute alcohol, refluenced in the presence of methyl iodide to obtain a mixture; cooling and acidifying the mixture with HCL, then extracting the mixture with EtOAc to obtain organic layers; combining the organic layers, drying and concentrating the organic layers to produce 2-Acetyl-4,6,6-trimethylcyclonhexa-1,3,5-trione;

b) Selectively methoxylating 2-Acetyl-4,6,6-trimethylcyclonhexa-1,3,5-trione to obtain 2-Acetyl-5-methoxy-4,6,6-trimethylcyclonhexa-1,3-dione with −78° C. of the reaction temperature;

c) Stirring a solution of 2-Acetyl-5-methoxy-4,6,6-trimethylcyclonhexa-1,3-dione in EtOH and 50% KOH in water and benzaldehyde at room temperature to obtain a mixture; extracting the mixture, washing the mixture with water, following by drying, concentrating, isolating and recrystallizing the mixture to obtain 2-[(1'-hydroxy-2'-ene-3'-phenyl)propenylene]-5-methoxy-4,6,6-trimethyl-1,3-cyclohexene(4,5)-dione.

Thus, the present invention includes four parts: first, the total synthesis (route) of desmosdumotin C; second, the derivates of dusmosdumotin C and their synthesis methods (routes); third, intramolecular cyclizatized compounds represented by desmosdumotin B and their synthesis methods (routes); forth, the use of these compounds as anti-tumor and/or anti-HIV agents.

DETAILED DESCRIPTION OF THE INVENTION

First Part: the Total Synthesis of Desmosdumotin C.

Desmosdumotin C was synthesized from 2,4,6,-trihydroxyacctophenone 2,4,6,-trihydroxyacetophenone is refluenced with three equivalents of methyl iodide in the presence of sodium methoxide to obtain 2-acetyl-4,6,6-trimethylcyclonhexa-1,3,5-trione in 56% yield along with tetramethyl production in 9% yield. The selective methoxylation of 2-acetyl-4,6,6-trimethylcyclonhexa-1,3,5-trione was achieved in medium yield by treatment with TMSCHN2 at the temperature of −78° C. Employing a higher temperature gave a low yield of the desired compound without increasing reaction selectivity. The use of other conditions could not get the target compound because of the presence of a strongly acidic proton on the C-6 position.

Finally, desmosdumotin C was obtained in 54% yield by the reaction with benzaldehyde in 50% KOH aqueous solution with the mixture of two exchanged isomers by the ratio of 13:1. The main isomer is obtained from the recrystallization from $CHCl_3$-MeOH as yellow needles.

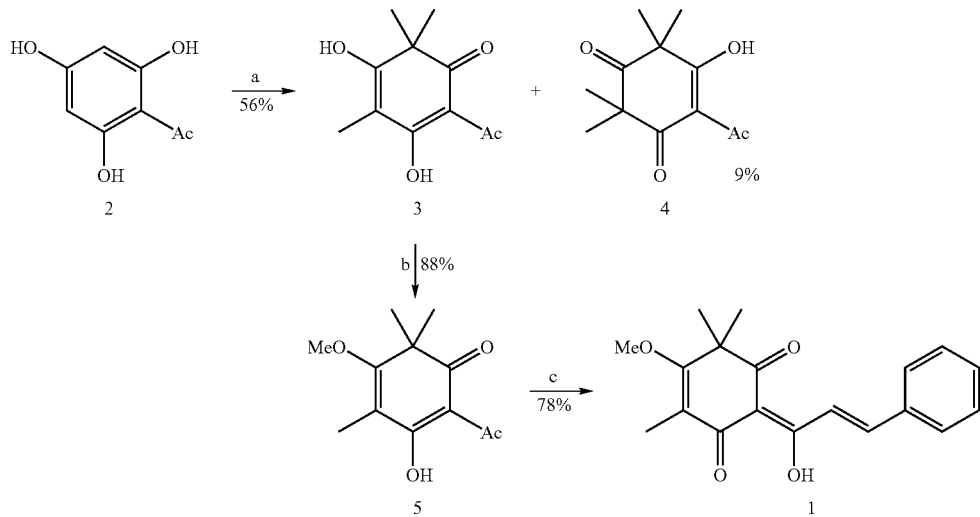

Second Part: the Derivates of Desmosdmnotin C and their Synthesis Routes.

I. The Structure of Derivates of Desmosdumotin C of the Present Invention was Shown as Formula (I):

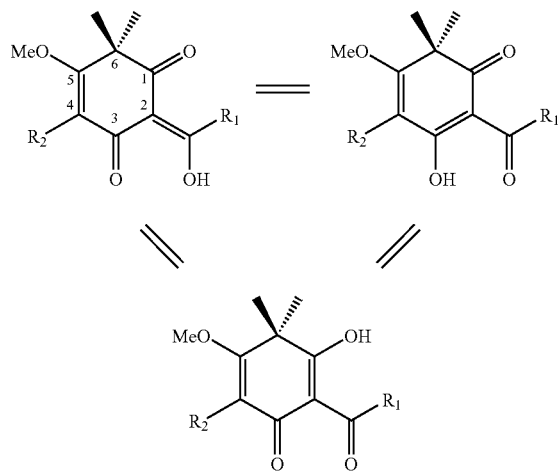

Wherein $R_1=C_2\text{-}C_8R_1'$, $R_2$ is hydrogen, lower saturated or unsaturated alkyl, halogen, hydroxyl, alcoxyl, aryl, substituted aryl, substituted heterocycle.

Wherein C2-C8 is saturated or unsaturated alkyl.

Wherein $R_1'$ is selected from the groups consisting of aromatic ring; substituted aromatic ring with the group selecting from halogen, hydroxyl, lower alkyl, alkoxyl, furyl, thienyl, and thiazoly; unsaturated aromatic heterocyclic ring; and substituted aromatic heterocyclic ring with the group selecting from halogen, hydroxyl, lower alkyl, alkoxyl, furyl, thienyl, and thiazoly.

wherein $R_1$ is preferably —$CH_2$=$CH_2R_1'$, wherein $R_1'$ is selected from the groups consisting of aromatic ring; substituted aromatic ring with the group selecting from halogen, hydroxyl, lower alkyl, alkoxyl, furyl, thienyl, and thiazoly; unsaturated aromatic heterocyclic ring; and substituted aromatic heterocyclic ring with the group selecting from halogen, hydroxyl, lower alkyl, alkoxyl, furyl, thienyl, and thiazoly. More preferably, $R_1'$ is selected from the group consisting of 4-bromophenyl, 4-chlorophenyl, 4-iodophenyl, hydroxy substituted phenyl, lower alkyl substituted phenyl, alkoxy substituted phenyl, 2-furyl, 2-thiophene, and 2-thiazoly.

The compounds with the formula (II) and (III) was obtained by the intramolecular cyclization of $R_1$ with position 2-carbonyl.

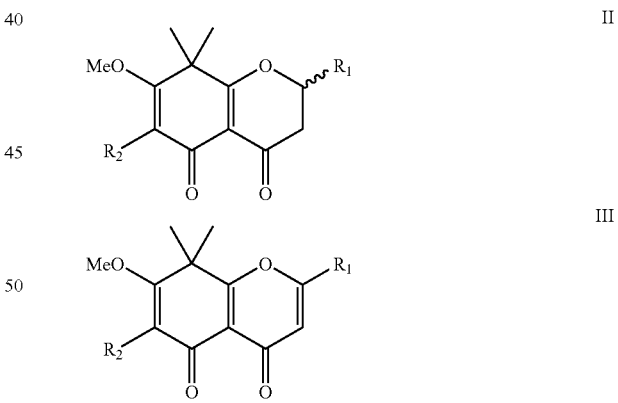

II. Synthesis Routes

The present invention relates to the synthesis method of desmosdumotin C derivates. Desmosdumotin C was treated as novel leading structure. Its derivates may become the antitumor-promoting agents.

By using other aromatic aldehydes rather than benzaldehyde in the final step, various derivates of desmosdumotin C could be obtained; chemical modification of A cycle may get another derivates. Some of the derivates may obtain by the following routes:

Scheme A

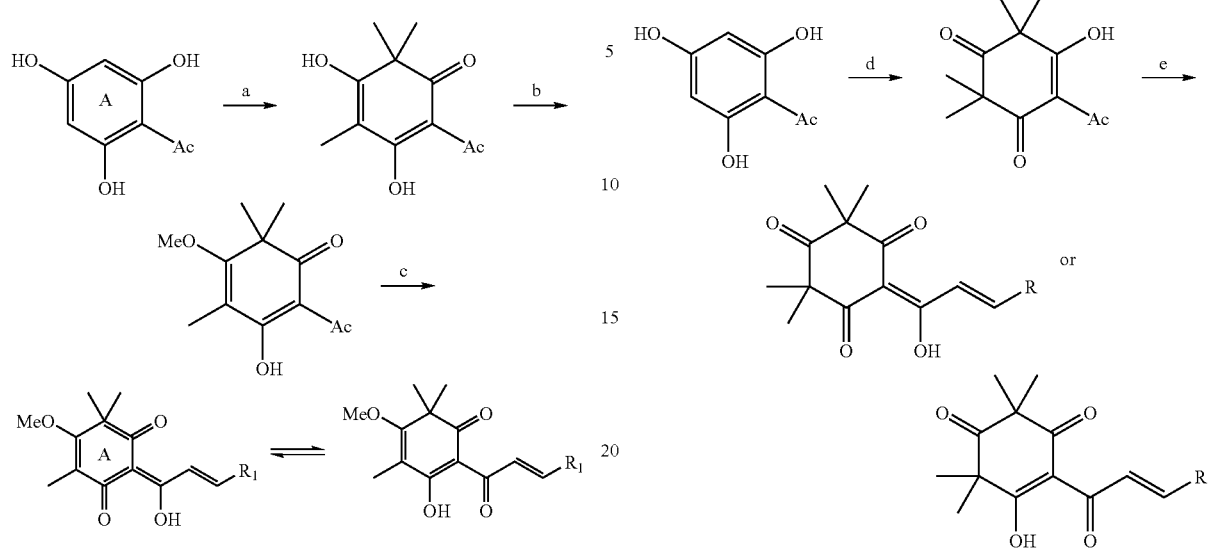

In the scheme A, reaction was initiated form 2,4,6,-trihydroxyacctophenone, desmodumotin C was get in the three steps. In the final step, using other aromatic aldehydes rather than benzaldehyde, various derivates of desmosdumotin C could be obtained.

Then, the intramolecular cyclization of these derivates may be conducted and other derivates could be obtained.

Scheme B, some derivates of desmosdumotin C may be obtained by the following route:

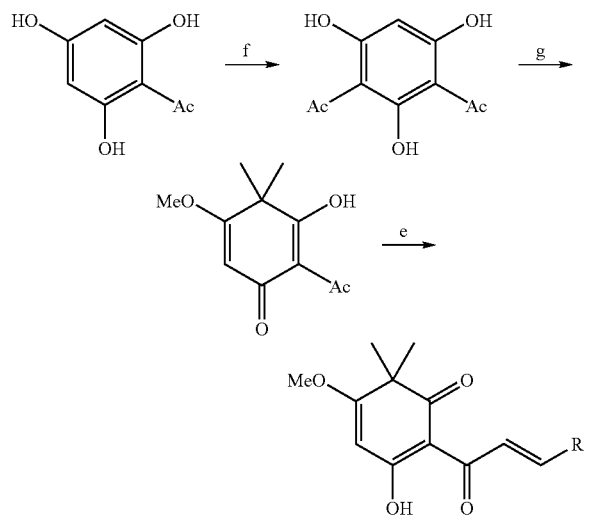

Acetylation of 2,4,6,-trihydroxyacctophenone monohydrate using a modified Marchand's reaction. After C-5 dialkyl was substituted, deacylation reaction was conducted in the presence of strong acid (concentrated H2SO4). Preferably, the substituent is methyl. The obtained compound was condensated with benzaldehyde under basic condition to obtain other derivates of desmodumotin C.

Scheme C, 2,4,6,-trihydroxyacctophenone was treated with excess MeI and NaOMe to obtain tetramethyl derivates.

In summary, the above synthesis methods of this invention include:

1. Reaction type: methylation, oxidation-reduction, substitution, acetylation, Marcband (aldol condensation), cyclization, and so on.
2. Reaction condition: general time: 2~4 hours; temperature: −78° C.

Third Part: The Total Synthesis Route of the Intramolecular Cyclization Compounds Represented by Dusmosdumotin B Total synthesis of desmosdumotin C and the derivates with different terminal aromatic ring or other structure were described above. Some active derivates represented by desmosdumotim B have the novel structures and had extraordinary A cycle or cyclization structure, which could be obtained by reaction of desmosdumotin C or other derivates in anhydrous DMSO with $I_2$ and concentrated $H_2SO_4$ (Scheme D), or be obtained by Michael reaction (Scheme E). Wherein R is hydrogen, lower saturated or unsaturated alkyl, halogen, hydroxyl, alkoxyl, aryl, substituted aryl or heterocycle.

Scheme D

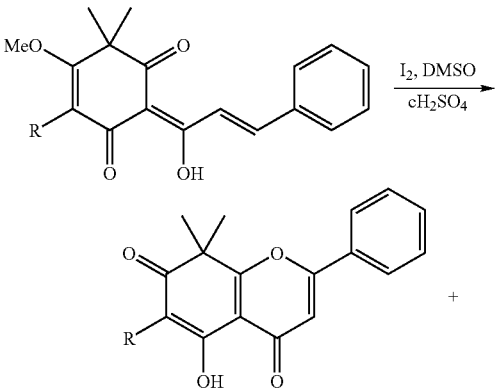

-continued

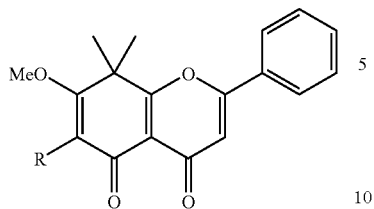
5

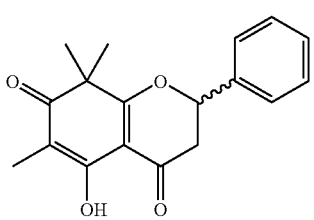
e

Scheme E

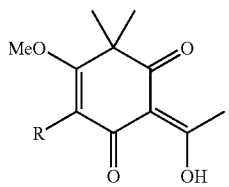

In these two methods, the following active compounds may be obtained:

a
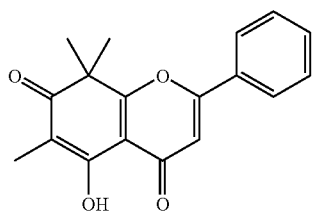

b
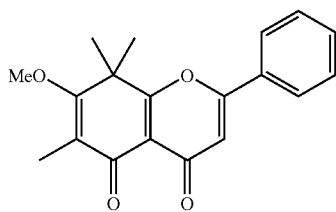

c
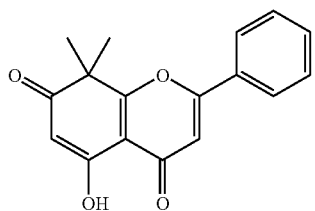

d
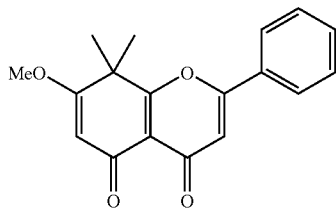

Wherein compound a is desmodumotin B. The synthetic desmosdumotin B has identical spectral data with those of the natural product We regarded desmosdumotin C was the possible biosynthetic precursor of desmosdumotin B.

Compound 4 showed the more significant anti-tumor activity than the leading compound based on its in vitro evaluation against a panel of several cancer cell lines, especially against 1A9 ovarian carcinoma with an $ED_{50}$ value of 0.7 μg/mL.

Forth Part: the Use of the Compounds as Anti-Tumor and/or Anti-HIV Agents.

Desmodumotin C and its derivates in this invention show the anti-tumor or antiviral activity in vitro evaluation. They also exhibited the inhibition of tumor growth in vivo with low toxicity.

Cancer cell used in cytotoxicity evaluation in vitro were all from human, including lung cancer cell line (A549), breast cancer cell line (MCF-7), ovarian cancer cell line (1A9), epidermoid nasopharyngeal carcinoma cell line (KB), vincristine-resistant cells (KB-VIN), melanoma cancer cell line (SK-MEL-2), ileocecal cancer cell line (HCT-8), renal carcinoma cell line (CAKI), bone cancer cell line (HOS), et al. the anti-cancer ability of the compound represented by half-effective amount ($ED_{50}$). Control drug was V16 (Etoposide).

The tumor activity in vitro testing represented by acute toxicity test and tumor-inhibiting testing of mice $S_{180}$, Method: $LD_{50}$ of desmosdumotin C to Kunming mice by vein route was obtained by the general acute toxicity test method. Sarcoma $S_{180}$ was hypodermic inoculated to mice, drug administrated, compared drug group with control group, inhibition rate was calculated, P value show the statistical difference. Result: intra $LD_{50}$ of Desmosdumotin C was above 46.0 mg/kg to both male and female mice in acute toxicity test. The inhibition rate of $S_{180}$ tumor growth were 47.02%, 43.16% and 30.18% in 10, 5, and 2.5 mg/kg dosage group respectively when treatment prescription was iv×10 qd. The result show desmosdumotin C has anti-tumor activity in three groups, Moreover weight decrease of mice in drug group was similar to the control group. This phenomenon indicated that desmosdumotin C was safety.

Anti-HIV ability of compound was showed by therapeutic index (TI), the test was operated as fowling steps: The T cell line, H9, was maintained in continuous culture with complete medium (RPMI 1640) with 10% fetal calf serum (FCS) supplemented with 1-glutamine at 5% $CO_2$ and 37° C. Test samples were first dissolved in dimethyl sulfoxide (DMSO). The following were the final drug concentrations routinely used for screening: 100, 20, 4 and 0.8 μg/mL. As the test samples were being prepared, an aliquot of the T cell line, H9, was infected with HIV-1, while another aliquot was mock-infected with complete medium. The stock virus used for these studies typically had a $TCID_{50}$ value of $10^4$ Infectious units/mL. The appropriate amount of virus for a multiplicity of infection between 0.1 and 0.01 infectious units/cell was added to the first aliquot of H9 cells, The other aliquot of H9 cells only received culture medium and then was incubated under identical conditions as the HIV-infected H9 cells. After a 4 h incubation at 37° C. and 5% $CO_2$, both cell populations were washed three times with fresh medium and then added to the appropriate wells of a 24-well-plate containing the various concentrations of the test drug or culture medium (positive infected control/negative drug control). In addition, AZT was also assayed during each experiment as a positive drug control. The plates were incubated at 37° C. and 5% $CO_2$ for 4 days. Cell-free supernatants were collected on day 4 for use in in-house P24 antigen ELISA assay. P24 antigen is a core protein of HIV and therefore is an indirect measure of virus present in the supernatants, thereby calculating the $EC_{50}$ of the compound for inhibiting HIV. $IC_{50}$ of the compound was determined by performing cell counts by a Coulter Counter on the mock-infected H19 cells, which had either received culture medium (no toxicity) or test sample or AZT. For example, Desmosdumotin D was demonstrated potent anti-HIV activity ($IC_{50}$=10.7 µg/mL, $EC_{50}$=0.022 µg/mL, TI=$IC_{50}$/$EC_{50}$=10.7/0.022=489). Lawinal also showed anti-HIV activity ($IC_{50}$=104 µg/mL, $EC_{50}$=2.30 µg/mL, TI=45.2.

According to the present invention, the present invention relates to a pharmaceutical compositions containing at least one compound mentioned above and pharmaceutically acceptable excipients or carrier. According to the present invention, the synthesized compound and its derivates could be formed to pharmaceutical compositions with any excipients or carrier. The composition could be administrated by oral route or parenteral route. The compounds and their derivates of the present invention could be obtained by the general methods in this field. The dosage form included but not limited the following: tablet, capsule, solution, suspension, granules, injection, transdermal drug delivery system and so on.

The present invention also relates to the use of at least one compound mentioned above in the treatment of tumor and/or HIV. Dosage could change from 0.5 to 10 mg/kg weight when the compounds used for mammal or human.

EXAMPLE

The following examples are illustrative but not limitative of the present invention.

Example 1

Synthesis of Desmosdumotin C and its Two Cyclization Derivates (Desmosdumotin B and Compound I)

Desmosdumotin C could be synthesized as scheme a-b-c, two cyclization derivates could be obtained based on the synthesis method of desmosdumotin B desmosdumotin B (7-hydroxyl-6,8,8-trimethyl-2-phenyl-8H-chromene-4,5-dione) compound I (7-methoxy-6,8,8-trimethyl-2-phenyl-8H-chromene-4,5-dione)

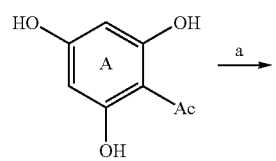

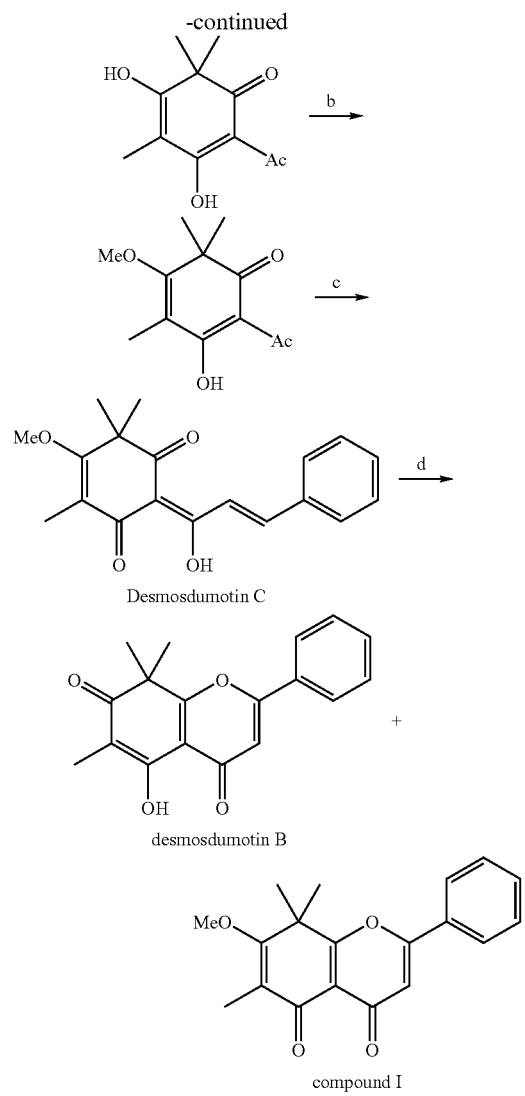

Desmosdumotin C desmosdumotin B compound I a) Dissolving 2,4,6,-trihydroxyacetophenone (1,487 mg, 2.9 mmol) with methyl iodide (1.95 ml, 3.7 mmol) in the presence of MeOH (3 ml) and sodium methoxide (0.6 ml, 3.3 mmol) to obtain a mixture. The mixture was cooled and acidified with HCL, then extracted with EtOAc for three times to obtain organic layers; the organic layers were combined, dried and concentrated to obtain a residue. The residue was chromatographed on silica gel with EtOAC-hexane (1:9 to 1:4, v/v) as an eluent to produce 2-Acetyl-4,6,6-trimethylcyclonhexa-1,3,5-trione in 56% yield.

b) The selective methoxylation of 2-Acetyl-4,6,6-trimethyl-cyclonhexa-1,3,5-trione was performed at low temperature (−78° C.). A solution of TMSCHN$_2$ (2M) was added to a solution (2:1, 6 ml) of 2-Acetyl-4,6,6-trimethylcyclon-hexa-1,3,5-trione (412 mg, 1.96 mmol). Acetic acid was then added to the solution to dissolve the excess TMSCHN2 to obtain a mixture. The mixture was extracted with EtOAc for three times to obtain an extract, the extract was combined, dried over $Na_2SO_4$ and concentrated in vacuum to obtain a residue, the residue was purified by silica-gel c column chromatography with EtOAc-hexane (1:2) as an eluent to obtain the methylated compound, 2-Acetyl-5-methoxy-4,6,6-trimethylcyclonhexa-1,3-dione in 61% yield.

c) A solution of 2-Acetyl-5-methoxy-4,6,6-trimethylcyclonhexa-1,3-dione (72 mg, 0.32 mmol) and 50% KOH (1 ml) in water and benzaldehyde (0.1 ml, 0.99 mmol) was stirred at room temperature to obtain a mixture. The mixture was extracted with dichloromethane to obtain an extract. The extract was washed with water, dried, concentrated, chromatographed on silica gel and recrystallized to obtain 2-[(1'-hydroxy-2'-ene-3'-phenyl)propenylene]-5-methoxy-4,6,6-trimethyl-1,3-cyclohexene (4,5)-diketone (desmosdumotin C).

d) To a solution of desmosdumotin C (97 mg, 0.31 mmol) in anhydrous DMSO (3 mL), 0.5 v/w % of 12 in DMSO (1 mL, 0.02 mmol of I2) and concentrated $H_2SO_4$ were added droplet to obtain a reaction mixture. The reaction mixture was heated for 1 h. An additional identical portion of concentrated $H_2SO_4$ was added droplet to the mixture. After 1.5 h, the reaction mixture was quenched with ice-cold aqueous 10% $Na_2S_2O_3$ and extracted with EtOAc to obtain an extract. The extract was washed with water, dried to obtain a residue. The residue was chromatographed on silica gel to obtain desmosdumotin B (30 mg, 33% yield) and compound I (52 mg, 54% yield).

The physical parameter of Desmosdumotin B: Pale yellow prisms, mp: 224-224.5° C. ($CH_2Cl_2$-hexane) (lit. 217-218° C.). IR (KBr): 1669, 1633, 1602, 1553, 1454, 1432, 1300, 1162, 873 cm$^{-1}$. $^1$H NMR ($CDCl_3$): δ13.1 (s, 1H, chelated-OH), 7.84-7.77 (m, 2H, Ar-2',6'-H), 7.66-7.53 (m, 3H, Ar-3', 4',5'-H), 6.90 (s, 1H, 3-H), 1.88 (s, 3H, 6-$CH_3$), 1.59 (s, 6H, 8-$CH_3$X2). MS m/z 297 (M$^+$+1), 282 (7) (M$^+$+1-$CH_3$), 269 (3) (M$^+$+1-CO).

The physical parameter of compound I: Pale yellow prisms, mp: 212-213° C. (EtOAc-hexane). IR (KBr): 1675, 1405, 1124 cm$^{-1}$. $^1$H NMR ($CDCl_3$): δ7.80-7.74 (m, 2H, Ar-2',6'-H), 7.58-7.50 (m, 3H, Ar-3',4',5'-H), 6.84 (s, 1H, 3-H), 3.96 (s, 3H, 7-$OCH_3$) 1.99 (s, 3H, 6-$CH_3$), 1.65 (s, 6H,8-$CH_3$X2). MS m/z 311 (M$^+$+1).

Example 2

Total Synthesis of 2-[1'-Hydroxy-3-(4-bromophenyl)-allylidene]-5-methoxy-4,6,6-trimethylcyclohex-4-ene-1,3-dione (compound 2)

The synthesis method was same with example 1 except that the temperature was −78° C. in step b) and in step c), a solution of 2-Acetyl-4,6,6-trimethylcyclonhexa-1,3-dione in alcohol (72 mg, 0.32 mmol) is stirred with 50% KOH in water, 4-bromrophenylaldenyde benzaldehyde (RCHO) (0.1 ml, 0.99 mmol) at room temperature to obtain a mixture. The mixture was extracted with dichloromethane to obtain an extract. The extract was washed with water, dried, concentrated, isolated and recrystallized to obtain the compound 2 (one of derivates of desmosdumotin C).

The physical parameter of compound 2, 2-[1'-Hydroxy-3-(4-bromphenyl)-allylidene]-5-methoxy-4,6,6-trimethylcyclohex-4-ene-1,3-dione: IR (KBr): 2976, 2935, 1657, 1623, 1517, 1488, 1468, 1429 cm$^{-1}$. 1H-NMR (CDCl3): 19.20 (s) and 18.66 (s) (11:1, 1H, chelated-OH), 8.51 (d) and 8.30 (d) (1:11, 1H, J=15.9 Hz, trans-olefinic proton), 7.84 (d) and 7.83 (d) (1:11, 1H, J=15.9 Hz, trans-olefinic proton), 7.56-7.48 (m, 4H, Ar-2",3",5",6"-H), 3.95 (s) and 3.88 (s) (11:1, 3H, 5-OCH3), 1.99 (s) and 1.94 (s) (11:1, 3H, 4-CH3), 1.46 (s) and 1.36 (s) (1:11, 6H, 6-$CH_3$x2). MS m/z 391 and 393 (M+, 1:1).

Example 3

Synthesis of 2-[1'-Hydroxy-3-(2-methoxyphenyl)-allylidene]-5-methoxy-4,6,6-trimethylcyclohex-4-ene-1,3-dione (compound 3)

The synthesis method was same with example 1 except the step c), a solution of 2-Acetyl-5-methoxy-4,6,6-trimethylcyclonhexa-1,3-dione in alcohol is stirred with 50% KOH in water, 2-methoxyphenylaryladehyde (RCHO) at room temperature to obtain a mixture. The mixture was extracted with dichloromethane to obtain an extract. The extract was washed with water, dried, concentrated, isolated and recrystallized to obtain the compound 3 (one of derivates of desmosdumotin C).

The physical parameter of compound 3, 2-[1'-Hydroxy-3-(2-methoxyphenyl)-allylidene]-5-methoxy-4,6,6-trimethyleylohex-4-ene-1,3-dione: IR (KBr): 2976, 2938, 1657, 1615, 1513, 1487, 1465, 1423, 1246 cm$^{-1}$. $^1$H-NMR ($CDCl_3$): 19.16 (s) and 18.82 (s) (2.5:1, 1H, chelated-OH), 8.54 (d) and 8.38 (d) (1:2.5, 1H, J=15.5 Hz, trans-olefinic proton), 8.39 (d) and 8.31 (d) (1:2.5, 1H, J=15.5 Hz, trans-olefinic proton), 7.79 (dd) and 7.76 (dd) (1:2.5, 1H, J=6.9 and 1.2 Hz, Ar-6"-H), 7.37 (ddd) and 7.35 (ddd) (1:2.5, 1H, J=8.2, 6.9 and 1.2 Hz, Ar-4"-H), 7.00-6.87 (m, 2H, Ar-3",5"-H), 3.94 (s) and 3.90 (s) (2.5:1, 3H, 5-$OCH_3$), 3.89 (s) and 3.87 (s) (2.5:1, 3H, Ph-$OCH_3$), 1.98 (s) and 1.94 (s) (2.5:1, 3H, 4-$CH_3$), 1.45 (s) and 1.36 (s) (1:2.5, 6H, 6-$CH_3$X2). MS m/z 343 (M$^+$+1).

Example 4

Synthesis of 2-[1'-Hydroxy-3-(3-methoxyphenyl)-allylidene]-5-methoxy-4,6,6-trimethyl-cyclohex-4-ene-1,3-dione (compound 4)

The synthesis method was same with example 1 except that the temperature was −50° C. in step b) and in step c), a solution of 2-Acetyl-5-methoxy-4,6,6-trimethylcyclonhexa-1,3-dione in alcohol is stirred with 50% KOH in water, 3-methoxyphenylaryladehyde (RCHO) at room temperature to obtain a mixture. The mixture was extracted with dichloromethane to obtain an extract. The extract was washed with water, dried, concentrated, isolated and recrystallized to obtain the compound 4 (one of derivates of desmosdumotin C).

The physical parameter of compound 4, 2-[1'-Hydroxy-3-(3-methoxyphenyl)-allylidene]-5-methoxy-4,6,6-trimethyl-cyclohex-4-ene-1,3-dione: IR (KBr): 2976, 2938, 1656, 1624, 1580, 1514, 1450, 1425, 1256 cm$^{-1}$. $^1$H-NMR ($CDCl_3$): 19.16 (s) and 18.75 (s) (3.5:1, 1H, chelated-OH), 8.50 (d) and 8.29 (d) (1:3.5, 1H, J=15.5 Hz, trans-olefinic proton), 7.91 (d) and 7.89 (d) (1:3.5, 1H, J=15.5 Hz, trans-olefinic proton), 7.34-7.12 (m, 3H, Ar-2",5",6"-H), 6.98-6.90 (m, 2H, Ar-4"-H), 3.95 (s) and 3.88 (s) (3.5:1, 3H, 5-$OCH_3$), 3.84 (s, 3H, Ph-$OCH_3$), 1.99 (s) and 1.94 (s) (3.5:1, 3H, 4-$CH_3$), 1.46 (s) and 1.37 (s) (1:3.5, 6H, 6-$CH_3$X2). MS m/z 343 (M$^+$+1).

Example 5

Synthesis of 2-[1'-Hydroxy-3-(4-methoxyphenyl)-allylidene]-5-methoxy-4,6,6-trimethyl-cyclohex-4-ene-1,3-dione (compound 5)

The synthesis method was same with example 1 except the step c), a solution of 2-Acetyl-5-methoxy-4,6,6-trimethylcyclonhexa-1,3-dione in alcohol is stirred with 50% KOH in water, 4-methoxyphenylarylaldehyde (RCHO) at room temperature to obtain a mixture. The mixture was extracted with dichloromethane to obtain an extract. The extract was washed with water, dried, concentrated, isolated and recrystallized to obtain the compound 5 (one of derivates of desmosdumotin C).

The physical parameter of compound 5, 2-[1'-Hydroxy-3-(4-methoxyphenyl)-allylidene]-5-methoxy-4,6,6-trimethyl-cyclohex-4-ene-1,3-dione: IR (KBr): 2975, 2934, 1656, 1621, 1600, 1572, 1510, 1423, 1243, 1171 cm$^{-1}$. $^1$H-NMR (CDCl$_3$): 19.19 (s, 1H, chelated-OH), 8.23 (d, 1H, J=15.5 Hz, trans-olefinic proton), 7.94 (d, 1H, J=15.5 Hz, trans-olefinic proton), 7.68-7.61 (m, 2H, Ar-2", 6"-H), 6.95-6.87 (m, 2H, Ar-3", 5"-H), 3.95 (s, 3H, 5-OCH$_3$), 3.85 (s, 3H, Ph-OCH$_3$), 2.00 (s, 3H, 4-CH$_3$), 1.38 (s, 6H, 6-CH$_3$X2). MS m/z 343 (M$^+$+1).

Example 6

Synthesis of 2-[1'-Hydroxy-3-(4-hydroxyphenyl)-allylidene]-5-methoxy-4,6,6-trimethyl-cyclohex-4-ene-1,3-dione (compound 6)

The synthesis method was same with example 1 except that the step c), a solution of 2-Acetyl-5-methoxy-4,6,6-trimethylcyclonhexa-1,3-dione in alcohol is stirred with 50% KOH in water, 4-hydroxyphenylarylaldehyde (RCHO) at room temperature to obtain a mixture. The mixture was extracted with dichloromethane to obtain an extract. The extract was washed with water, dried, concentrated, isolated and recrystallized to obtain the compound 6 (one of derivates of desmosdumotin C).

The physical parameter of compound 6, 2-[1'-Hydroxy-3-(4-hydroxyphenyl)-allylidene]-5-methoxy-4,6,6-trimethyl-cyclohex-4-ene-1,3-dione: IR (KBr): 2359, 2331, 1647, 1619, 1600, 1518, 1446, 1415, 1148, 830, 771 cm$^{-1}$. $^1$H-NMR (CDCl$_3$): 19.15 (s) and 18.81 (s) (2:1, 1H, chelated-OH), 8.32 (d) and 8.14 (d) (1:2, 1H, J=15.7 Hz, trans-olefinic proton), 7.91 (d) and 7.89 (d) (1:2, 1H, J=15.7 Hz, trans-olefinic proton), 7.54 (d) and 7.53 (d) (1:2, 2H, J=8.6 Hz, Ar-2",6"-H), 6.82 (d) and 6.81 (d) (1:2, 2H, J=8.6 Hz, Ar-3", 5"-H), 3.91 (s) and 3.85 (s) (2:1, 3H, 5-OCH$_3$), 2.36 (br s, 1H, Ph-OH), 1.95 (s) and 1.91 (s) (2:1, 3H, 4-CH$_3$), 1.42 (s) and 1.33 (s) (1:2, 6H, 6-CH$_3$X2). MS m/z 327 (M$^+$−1).

Example 7

Synthesis of 2-(3'-Furan-2"-yl-1'-hydroxy-allylidene)-5-methoxy-4,6,6-trimethyl-cyclohex-4-ene-1,3-dione (compound 7)

The synthesis method was same with example 1 except that the step c), a solution of 2-Acetyl-5-methoxy-4,6,6-trimethylcyclonhexa-1,3-dione in alcohol is stirred with 50% KOH in water, 2-furanaryladehyde (RCHO) at room temperature to obtain a mixture. The mixture was extracted with dichloromethane to obtain an extract. The extract was washed with water, dried, concentrated, isolated and recrystallized to obtain the compound 7 (one of derivates of desmosdumotin C).

The physical parameter of compound 7, 2-(3'-Furan-2"-yl-1'-hydroxy-allylidene)-5-methoxy-4,6,6-trimethyl-cyclohex-4-ene-1,3-dione: IR (KBr): 3120, 2986, 2945, 1654, 1626, 1558, 1502, 1442, 1414 cm$^{-1}$. $^1$H-NMR (CDCl$_3$): 19.07 (s) and 18.71 (s) (2.2:1, 1H, chelated-OH), 8.35 (d) and 8.15 (d) (1:2.2, 1H, J=15.7 Hz, trans-olefinic proton), 7.73 (d) and 7.68 (d) (1:2.2, 1H, J=15.7 Hz, trans-olefinic proton), 7.54 (d) and 7.52 (d) (1:2.2, 1H, J=0.8 Hz, Ar-5"-H), 6.75 (d) and 6.72 (d) (1:2.2, 1H, J=3.1 Hz, Ar-3"-H), 6.50 (dd) and 6.48 (dd) (1:2.2, 1H, J=3.1 and 0.8 Hz, Ar-4"-H), 3.94 (s) and 3.87 (s) (2.2:1, 3H, 5-OCH$_3$), 1.98 (s) and 1.94 (s) (2.2:1, 3H, 4-CH$_3$), 1.45 (s) and 1.36 (s) (1:2.2, 6H, 6-CH$_3$X2). MS m/z 303 (M$^+$+1).

Example 8

Synthesis of 2-(1'-Hydroxy-3'-thiophen-2"-yl-allylidene)-5-methoxy-4,6,6-trimethyl-cyclohex-4-ene-1,3-dione (compound 8)

The synthesis method was same with example 1 except that the step c), a solution of 2-Acetyl-5-methoxy-4,6,6-trimethylcyclonhexa-1,3-dione in alcohol is stirred with 50% KOH in water, 2-thiophenecarboxaldehyde (RCHO) at room temperature to obtain a mixture. The mixture was extracted with dichloromethane to obtain an extract. The extract was washed with water, dried, concentrated, isolated and recrystallized to obtain the compound 8 (one of derivates of desmosdumotin C).

The physical parameter of compound 8, 2-(1'-Hydroxy-3'-thiophen-2"-yl-allylidene)-5-methoxy-4,6,6-trimethyl-cyclohex-4-ene-1,3-dione: IR (KBr): 3083, 2978, 2934, 1655, 1607, 1521, 1501, 1467, 1447, 1408, 1199, 1150 cm$^{-1}$. $^1$H-NMR (CDCl$_3$): 19.17 (s) and 18.79 (s) (2.5:1, 1H, chelated-OH), 8.34 (d) and 8.15 (d) (1:2.5, 1H, J=15.6 Hz, trans-olefinic proton), 8.08 (d) and 8.05 (d) (1:2.5, 1H, J=15.6 Hz, trans-olefinic proton), 7.49-7.34 (m, 2H, Ar-3",5"-H), 7.11-7.04 (m, 1H, Ar-4"-H), 3.94 (s) and 3.87 (s) (2.5:1, 3H, 5-OCH$_3$), 1.98 (s) and 1.94 (s) (2.5:1, 3H, 4-CH$_3$), 1.45 (s) and 1.36 (s) (1:2.5, 6H, 6-CH$_3$X2). MS m/z 319 (M$^+$+1).

Example 9

Synthesis of 2-[(1'-Hydroxy-3'-thiazol-2-yl-allylidene)-5-methoxy-4,6,6-trimethyl-1,3-cyclohex-4-ene-1,3-dione (compound 9)

The synthesis method was same with example 1 except that the step c), a solution of 2-Acetyl-5-methoxy-4,6,6-trimethylcyclonhexa-1,3-dione in alcohol is stirred with 50% KOH in water, 2-thiazolecarboxaldehyde (RCHO) at room temperature to obtain a mixture. The mixture was extracted with dichloromethane to obtain an extract. The extract was washed with water, dried, concentrated, isolated and recrystallized to obtain the compound 8 (one of derivates of desmosdumotin C).

The physical parameter of compound 9, 2-[(1'-Hydroxy-3'-thiazol-2-yl-allylidene)-5-methoxy-4,6,6-trimethyl-1,3-cyclohex-4-ene-1,3-dione: IR (KBr): 3078, 2976, 2934, 1655, 1621, 1517, 1470, 1448, 1433, 1387, 1199, 1136, 974, 942 cm$^{-1}$. $^1$H-NMR (CDCl$_3$): 19.02 (s) and 18.50 (s) (2.5:1, 1H, chelated-OH), 8.65 (d) and 8.44 (d) (1:2.5, 1H, J=15.6 Hz, trans-olefinic proton), 8.03 (d) and 8.00 (d) (1:2.5, 1H, J=15.6 Hz, trans-olefinic proton), 7.98-7.92 (m, 1H, Ar-4"-H), 7.48-7.42 (m, 1H, Ar-5"-H), 3.96 (s) and 3.89 (s) (2.5:1, 3H, 5-OCH$_3$), 2.00 (s) and 1.94 (s) (2.5:1, 3H, 4-CH$_3$), 1.47 (s) and 1.37 (s) (1:2.5, 6H, 6-CH$_3$X2). MS m/z 320 (M$^+$+1).

Synthesis route of compounds 2~9 was in the following scheme:

2-[(1'-Hydroxy-3'-R-2-yl-allylidene)-5-methoxy-4,6,6-trimethyl-1,3-cyclohex-4-ene-1,3-dione

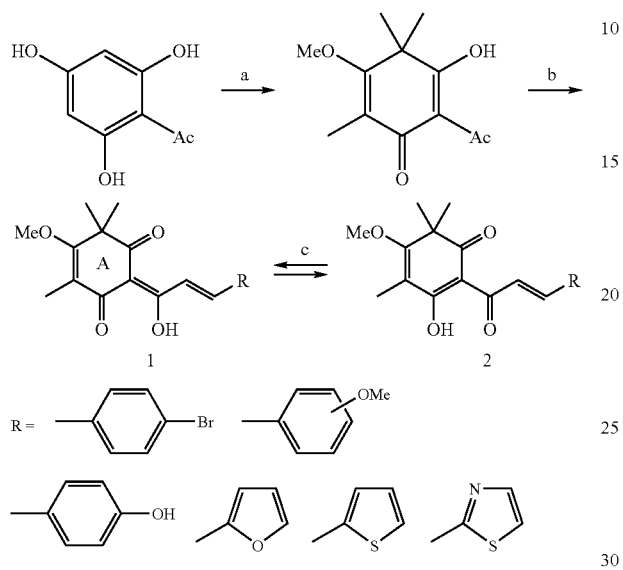

The structures of the compounds prepared by the above examples were shown as following:

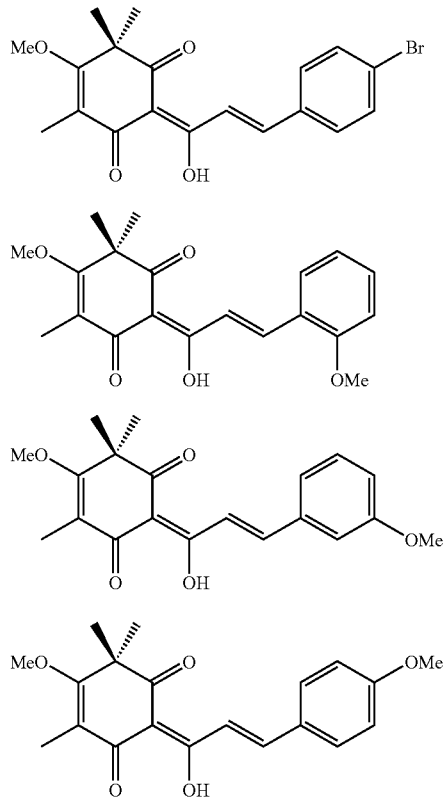

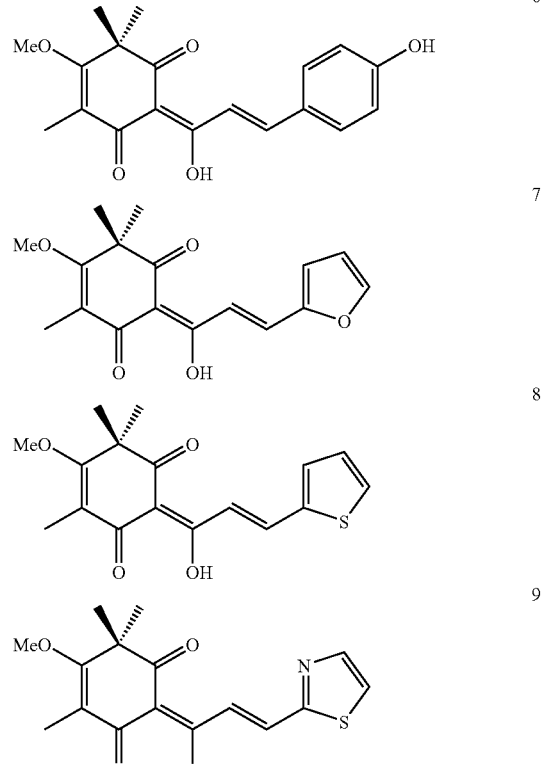

Compound 2 R: 4-bromophenyl; Compound 6 R: 4-hydroxyphenyl;
Compound 3 R: 2-methoxyphenyl; Compound 7 R: furan;
Compound 4 R: 3-methoxyphenyl; Compound 8 R: thiophen;
Compound 5 R: 4-methoxyphenyl; Compound 9 R: thiazol;

Example 10

7-hydroxyl-6,8,8-trimethyl-2-phenyl-2,3-dihydrogen-8H-chromene-4,5-dione (compound 11) and 2-[(1'-hydroxy-2'-ene-3'-phenyl)propenylene]-5-hydroxy-4,6,6-trimethyl-1,3-cyclohexene(4,5)-dione (compound 12)

Synthesis Route:

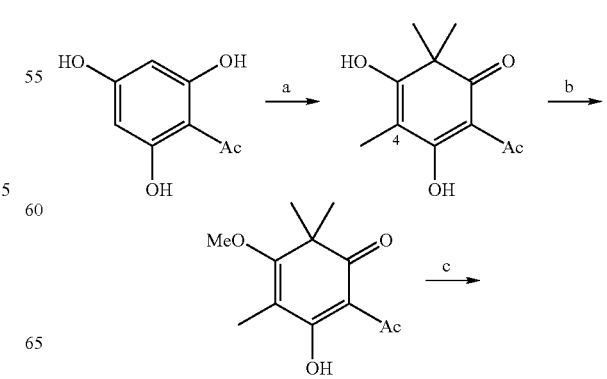

-continued

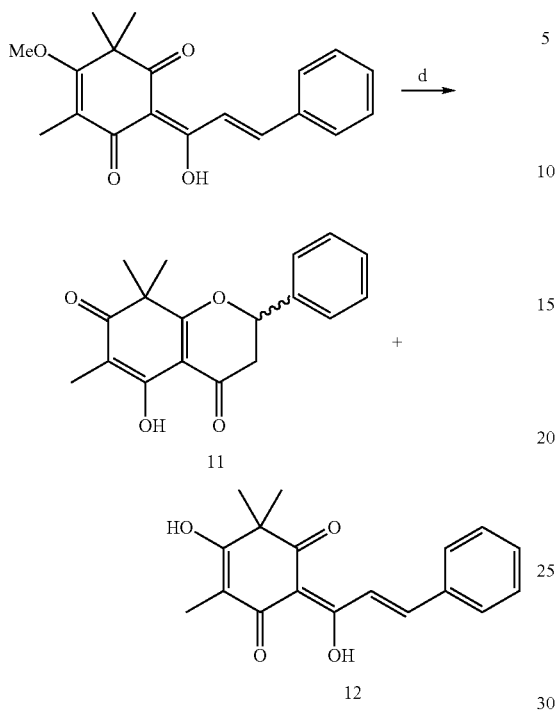

The synthesis method was same with example 1 except that to a solution of 2-[(1'-hydroxy-2'-ene-3'-phenyl)propenylene]-5-hydroxy-4,6,6-trimethyl-1,3-cyclohexene(4,5)-dione (94 mg, 0.30 mmol) in anhydrous acetone, MeOH (3 mL) and concentrated HCl (1 mL) was added to obtain a mixture. The mixture was refluxed for 1 h to obtain volatile solvents. After cooling, the volatile solvents were removed in vacuum to obtain a residue. The residue was partitioned between EtOAc and water to obtain an organic phase. The organic phase was washed with brine, dried over $Na_2SO_4$, and concentrated in vacuum to obtain a residue. The residue was chromatographed on silica gel with EtOAc-hexane (1:4-1:1, v/v) as an eluent to obtain compounds 11 (12 mg, 13% yield) and 12 (36 mg, 40% yield).

The physical parameter of Compound 11: Yellow powder, mp: 159-160.5° C. ($CH_2Cl_2$-hexane). IR (KBr): 2978, 2930, 2359, 1669, 1622, 1559, 1413, 1290, 1150 $cm^{-1}$. $^1$H-NMR ($CDCl_3$): 11.62 (s, 1H, OH, $D_2O$ disappeared), 7.52-7.38 (m, 5H, Ar—H), 5.58 (dd, 1H, J=13.8 and 3.8 Hz, 2-H), 3.10 (dd, 1H, J=17.3 and 13.8 Hz, 3-Hax), 2.88 (dd, 1H, J=17.3 and 3.8 Hz, 3-Heq), 1.81 (s, 3H, 5-$CH_3$), 1.45 (s, 3H, 8-$CH_3$), 1.41 (s, 3H, 8-$CH_3$). MS m/z 299 ($M^+$+1).

The physical parameter of Compound 12: Yellow powder, mp: 150-151° C. ($CH_2Cl_2$-hexane). IR (KBr): 3264 (br), 1621, 1510, 1447, 1470, 1433, 1230, 1117 $cm^{-1}$. $^1$H-NMR ($CDCl_3$): 19.19 (s) and 18.71 (s) (3:1, 1H, chelated-OH), 8.59 (d) and 8.33 (d) (1:3, 1H, J=15.4 Hz, trans-olefinic proton), 7.96 (d) and 7.92 (d) (1:3, 1H, J=15.4 Hz, trans-olefinic proton), 7.74-7.62 (m, 2H, Ar-2'',6''-H), 7.47-7.34 (m, 3H, Ar-3'',4'',5''-H), 5.89 (s) and 5.36 (s) (3:1, 1H, 5-OH, $D_2O$ disappeared), 1.93 (s) and 1.90 (s) (3:1, 3H, 4-$CH_3$), 1.54 (s) and 1.45 (s) (1:3, 3H, 6-$CH_3$X2). MS m/z 297 ($M^+$−1).

Example 11

2-[(1'-hydroxy-2'-ene-3'-phenyl)propenylene]-5-methoxy-4,6,6-trimethyl-1,3-cyclohexene(4,5)-diketone, (compound 13), and 7-methoxy-8,8-dimethyl-2-phenyl-8H-chromene-4,5-dione. (Compound 14)

Synthesis Route:

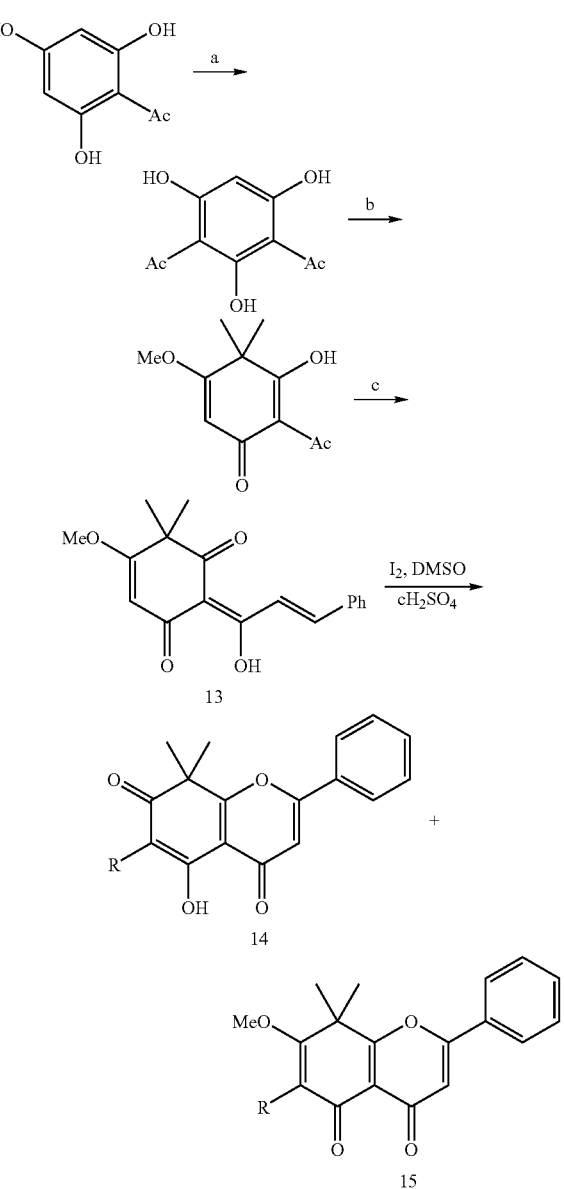

a) An improved Marchand reaction is conducted by using 2,4,6,-trihydroxyacctophenone as the initial material: 2,4,6,-trihydroxyacctophenone in AcOH was refluxed with $Ac_2O$ and $BF_3$ $OEt_2$ to obtain a mixture. The mixture was cooled to 0° C. and adjusted to pH 4 by NaOH, extracted by 5% MeOH/AcOEt to obtain organic layers, the organic layers were combined, dried in vacuum and dissolved in the MeOH to obtain a solution. The solution was stirred with NaOH at room temperature for 5 hours to obtain a product. The reaction was acidified with HCL, and then extracted with MeOH/AcOEt, the extract was washed by brine, dried and purified by silica to get 1,5-diacetyl-2,4,6-trihydroxybenzene.

b) 1,5-diacetyl-2,4,6-trihydroxybenzene was reacted with concentrated $H_2SO_4$ to obtain a mixture, the reaction mixture was methoxylated using $TMSCHN_2$, then extracted with MeOH/AcOEt to obtain 2-acetyl-5-methoxy-6,6-dimethylcyclohexane-1,3-dione.

c) A solution of 2-acetyl-5-methoxy-6,6-dimethylcyclohexane-1,3-diketone in EtOH aq KOH was reacted with benzaldehyde to obtain a mixture. The reaction mixture was extracted by dichloromethane, then washed by water, dried, concentrated, chromatographed on silica gel and crystallized to obtain compound 13.

d) To a solution of compound 13 in DMSO, $I_2$ and concentrated $H_2SO_4$ was added to obtain a mixture. The reaction mixture was heated for 1 hour. An additional identical portion of concentrated $H_2SO_4$ was added into the mixture to obtain an extract. The extract was washed with brine, dried over $Na_2SO_4$, and concentrated in vacuum to obtain a residue. The residue was chromatographed on silica gel to obtain compound 14 and 15.

Example 12

The result of activity of desmosdumotin C and its derivates (2~9) in vitro against human Tumor cell replication ($\mu mol\ L^{-1}$)

| | $ED_{50}$ ($\mu mol\ L^{-1}$) | | | | |
|---|---|---|---|---|---|
| | MCF-7 | A549 | IA9 | KB | KB-VIN |
| C | 12.75 | | 12.82 | 20.83 | 17.94 |
| 2 | | 3.57 | 2.80 | 4.33 | 4.84 |
| 3 | | 8.74 | 8.16 | 10.49 | 8.45 |
| 4 | | 8.16 | 8.45 | 9.62 | 6.99 |
| 5 | | 6.99 | 7.28 | 9.62 | 8.16 |
| 6 | | 9.48 | 8.86 | 11.62 | 11.62 |
| 7 | | 33.00 | 26.07 | 32.67 | 29.04 |
| 8 | | 14.10 | 12.53 | 17.24 | 10.65 |
| 9 | | 10.93 | 10.93 | 13.43 | 9.37 |

MCF-7: breast cancer
IA9: Human ovarian carcinoma
KB: Human epidermoid carcinoma of the nasopharynx
KB-VIN: multi-drug resistant expressing P-glycoprotein
A549: human lung carcinoma The result indicated that all the derivates were more active than the leading compound except compound 7. The activity of compound 3 is 4 times than desmosdumotin C.

Example 13

The Result of Activity of Desmosdumotin B and its Derivates (11-14) in Vitro Against Human Tumor Cell Replication

| | $ED_{50}$ ($\mu g \cdot mL^{-1}$) | | | | |
|---|---|---|---|---|---|
| compound | A549 | IA9 | MCF-7 | KB | KB-VIN |
| Desmosdumotin B | 28.0 | 36.0 | >5 | >40 | 2.0 |
| 11 | 13.5 | 8.0 | >5 | 10.5(44) | 7.5 |
| 12 | 9.0 | 8.0 | >5(25) | 10.5 | 6.5 |
| 13 | >5(48) | 3.63 | >5(47) | 4.1 | 2.9 |
| 14 | 2.0 | 0.7 | NA | 1.8 | 1.8 |
| 15 | 33.5 | 38.0 | >5(25) | 38.5 | 23.0 |

Desmosdumotin B illuminates significant activity against the KB-VIN cell line with an $ED_{50}$<2.0 $\mu gmL^{-1}$. Compound 14 illuminates strong and selective in vitro cytotoxic activity against IA9 ovarian carcinoma with ED50 value of 0.7 $\mu gmL^{-1}$.

Example 14

$LD_{50}$ of Desmosdumotin C to Kunming Mice by Single Vein Injection (Tablet)

| sex | Dosage mg/kg | Animal Number 只 | Death Distribution (day) 1 2 3 4 5 6 7 8 9 10---14 | Death Rate % | $LD_{50}$ (95% CL) mg/kg |
|---|---|---|---|---|---|
| male | 80 | 5 | 5 0 0 0 0 0 0 0 0 0 | 100 | |
| | 64 | 5 | 4 1 0 0 0 0 0 0 0 0 | 100 | |
| | 51.2 | 5 | 3 0 0 0 0 0 0 0 0 0 | 60 | |
| | 40.96 | 5 | 2 0 0 0 0 0 0 0 0 0 | 40 | |
| | 32.8 | 5 | 0 0 0 0 0 0 0 0 0 0 | 0 | |
| Female | 80 | 5 | 5 0 0 0 0 0 0 0 0 0 | 100 | |
| | 64 | 5 | 4 0 0 0 0 0 0 0 0 0 | 80 | |
| | 51.2 | 5 | 3 1 0 0 0 0 0 0 0 0 | 80 | |
| | 40.96 | 5 | 1 1 0 0 0 0 0 0 0 0 | 40 | |
| | 32.8 | 5 | 0 0 0 0 0 0 0 0 0 0 | 0 | |
| Half male/ half female | 80 | 10 | 10 0 0 0 0 0 0 0 0 0 | 100 | 46.0 (39.8~ 53.1) |
| | 64 | 10 | 8 1 0 0 0 0 0 0 0 0 | 90 | |
| | 51.2 | 10 | 6 1 0 0 0 0 0 0 0 0 | 70 | |
| | 40.96 | 10 | 3 1 0 0 0 0 0 0 0 0 | 40 | |
| | 32.8 | 10 | 0 0 0 0 0 0 0 0 0 0 | 0 | |

Example 15

The Result of Desmosdumotin C Inhibit the Growth of $S_{180}$ Tumor of Kunming Mice (Tablet)

| Group | Dasage mg/kg | Dosage Regimen | Animal Number Start/End | Tumor Weight Start/End | Weight X ± SD | Inhibition Rate % |
|---|---|---|---|---|---|---|
| Desmosdumotin C | 10 | iv × 10qd | 10/10 | 19.4/24.9 | 1.51 ± 0.21*** | 47.02 |

| Group | Dasage mg/kg | Dosage Regimen | Animal Number Start/ End | Weight Start/End | Tumor Weight X ± SD | Inhibition Rate % |
|---|---|---|---|---|---|---|
| | 5 | iv × 10qd | 10/10 | 19.7/25.3 | 1.62 ± 0.22*** | 43.16 |
| | 2.5 | iv × 10qd | 10/10 | 19.6/25.7 | 1.99 ± 0.18*** | 30.18 |
| CTX | 0.03 | iv × 7qd | 10/10 | 19.3/23.9 | 0.44 ± 0.14*** | 84.56 |
| Negative Control | Dissolvent | iv × 10qd | 20/20 | 19.1/26.4 | 2.85 ± 0.26 | |

Example 16

Preparation of Compound 2 Injection

Method: use the general technique in the art, NaCL (0.45 g) is dissolved and stirred with injection water (40 mL) to obtain a mixture. Then compound 2 (50 mg) was added into the mixture. pH was adjusted to 6.5-7.5 by 0.1N HCL. Sufficient water was added (to 50 mL) to obtain a mixture. The mixture was stirred and filtered, and filled in the neutral glass ampoule, sterilized for 30 min using 100° C. vapor.

What is claimed is:

1. A desmosdumotin compound having the formula (I)

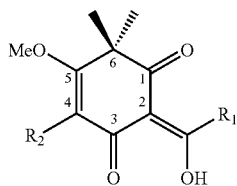

wherein
$R_1 = C_2\text{-}C_8 R^{1'}$,
$R_2$ is hydrogen, lower saturated or unsaturated alkyl, halogen, hydroxyl, alkoxyl, aryl, substituted aryl or heterocycle,
provided that $R_2$ is not

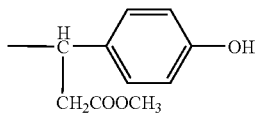

wherein $C_2$-$C_8$ is saturated or unsaturated alkyl that represents cis- and trans-isomer,
wherein $R_1'$ is selected from the groups consisting of aromatic ring; substituted aromatic ring with the group selecting from halogen, hydroxyl, lower alkyl, alkoxyl, furyl, thienyl, and thiazolyl; unsaturated aromatic heterocyclic ring; and substituted aromatic heterocyclic ring with the group selecting from halogen, hydroxyl, lower alkyl, alkoxyl, furyl, thienyl, and thiazolyl,
wherein $R_1$ is not styryl, isobutene, 1,2-dimethyl-1-propenyl, 1,2-dimethyl-phenylethane, 1,2-dibromo-phenethyl, and 2-hydroxy-styryl.

2. A compound of claim 1 wherein $R_1$ is —$CH_2$=$CH_2 R_1'$, wherein $R_1'$ is selected from the groups consisting of aromatic ring; substituted aromatic ring with the group selecting from halogen, hydroxyl, lower alkyl, alkoxyl, furyl, thienyl, and thiazolyl; unsaturated aromatic heterocyclic ring; or substituted aromatic heterocyclic ring with the group selecting from halogen, hydroxyl, lower alkyl, alkoxyl, furyl, thienyl, and thiazolyl,
wherein $R_1$ is not styryl, isobutene, 1,2-dimethyl-1-propenyl, 1,2-dimethyl-phenylethane, 1,2-dibromo-phenethyl, and 2-hydroxy-styryl.

3. A compound of claim 1, wherein $R_1'$ is selected from the group consisting of 4-bromophenyl, 4-chlorophenyl, 4-iodophenyl, hydroxy substituted phenyl, lower alkyl substituted phenyl, alkoxy substituted phenyl 2-furyl 2-thiophene, and 2-thiazolyl.

4. A compound of claim 1 selected from the group consisting of:
2-[1'-Hydroxy-3-(4-bromophenyl)-allylidene]-5-methoxy-4,6,6-trimethylcyclohex-4-ene-1,3-dione;
2-[1'-Hydroxy-3-(2-methoxyphenyl)-allylidene]-5-methoxy-4,6,6-trimethylcyclohex-4-ene-1,3-dione;
2-[1'-Hydroxy-3-(3-methoxyphenyl)-allylidene]-5-methoxy-4,6,6-trimethyl-cyclohex-4-ene-1,3-dione;
2-[1'-Hydroxy-3-(4-methoxyphenyl)-allylidene]-5-methoxy-4,6,6-trimethyl-cyclohex-4-ene-1,3-dione;
2-[1'-Hydroxy-3-(4-hydroxyphenyl)-allylidene]-5-methoxy-4,6,6-trimethyl-cyclohex-4-ene-1,3-dione;
2-[1'-Hydroxy-2-Furan-allylidene]-5-methoxy-4,6,6-trimethy-cyclohex-4-ene-1,3-dione;
2-[1'-Hydroxy-2-thiophen-allylidene]-5-methoxy-4,6,6-trimethyl-cyclohex-4-ene-1,3-dione;
2-[1'-Hydroxy-2-thiazol-allylidene)-5-methoxy-4,6,6-trimethyl-cyclohex-4-ene-1,3-dione.

5. A method for preparing a compound having the formula (I)

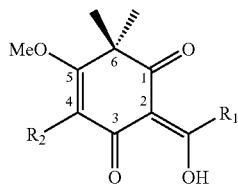

wherein
$R_1 = C_2\text{-}C_8 R^{1'}$,
$R_2$ is hydrogen, lower saturated or unsaturated alkyl, halogen, hydroxyl, alkoxyl, aryl, substituted aryl or heterocycle, provided that $R_2$ is not

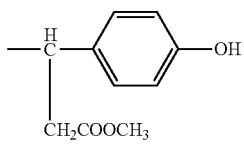

wherein $C_2$-$C_8$ is saturated or unsaturated alkyl that represents cis- and trans-isomer, wherein $R_1'$ is selected from the groups consisting of aromatic ring; substituted aromatic ring with the group selecting from halogen, hydroxyl, lower alkyl, alkoxyl, furyl, thienyl, and thiazolyl; unsaturated aromatic heterocyclic ring; and substituted aromatic heterocyclic ring with the group selecting from halogen, hydroxyl, lower alkyl, alkoxyl, furyl, thienyl, and thiazolyl, wherein $R_1$ is not styryl, isobutene, 1,2-dimethyl-1-propenyl, 1,2-dimethyl-phenylethane, 1,2-d ibromo-phenethyl, and 2-hydroxy-styryl, comprising the steps of:

a) Dissolving 2,4,6,-trihydroxyacctophenone and sodium methoxide in absolute alcohol, refluxing the 2,4,6,-trihydroxyacctophenone and sodium methoxide in the presence of methyl iodide to obtain a mixture; cooling and acidifying the mixture with HCL, then extracting the mixture with EtOAc to obtain organic layers; combining the organic layers, following by drying and concentrating the organic layers to produce 2-Acetyl -4,6,6-trimethylcyclonhexa-1,3,5-trione;

b) Selectively methoxylating 2-Acetyl -4,6,6-trimethylcyclonhexa-1,3,5-trione to obtain 2-Acetyl -5-methoxy-4,6,6-trimethylcyclonhexa-1,3-dione with −78° C. of the reaction temperature;

c) Stirring a solution of -Acetyl-5-methoxy-4,6,6-trimethylcyclonhexa-1,3-dione in EtOH and 50% KOH in water and benzaldehyde at room temperature to obtain a mixture; extracting the mixture, washing the mixture with water, following by drying, concentrating, isolating and recrystallizing the mixture to obtain 2-[(1'-hydroxy-2'-ene-3'-phenyl)propenylene]-5-methoxy-4,6,6-trimethyl -1,3-cyclohexene(4,5)-dione.

6. A method according to claim 5, further comprising the step of:

substituting the benzaldehyde in the step C by using the groups selecting from: 4-bromophenylaldehyde, o-, p-, and m-anisaledhyde, 2-furaldehyde, 2-thiophenecarboxaldehyde, and 2-thiazolecarboxaldehyde.

7. A method for preparing a compounds of claim 1 comprising the steps of:

a) Stirring 2,4,6,-trihydroxyacctophenone in AcOH, and refluxing the 2,4,6,-trihydroxyacctophenone in AcOH in presence of $Ac_2O$ and $BF_3OEt_2$ to obtain a mixture; cooling and adjusting the mixture to pH 2-6 by NaOH, extracting the mixture by 5% MeOH/AcOEt to obtain organic layers, combining the organic layers, following by drying in vacuum to obtain a product; dissolving the product in the MeOH and refluxing the product in MeOH in presence of NaOH at room temperature to obtained a refluxed product; acidifying the refluxed product with HCL, then extracted the refluxd product with MeOH/AcOEt to obtain an extract, washing the extract, following by drying and purifying by silica gel column to obtain 1,5-Diacetyl -2,4,6-trihydroxybenzene;

b) Conducting a strong redox of 1,5-Diacetyl-2,4,6-trihydroxybenzene with concentrated $H_2SO_4$ to obtain a mixture, methoxylated the mixture with $TMSCHN_2$, then extracting the mixture with MeOH/AcOEt to obtain 2-acetyl-5-methoxy-6,6-dimethylcyclohexane-1,3-dione;

c) Reacting a solution of 2-acetyl-5-methoxy-6,6-dimethylcyclohexane-1,3-dione in EtOH aq KOH with benzaldehyde to obtain an extract; washing, drying, concentrating, isolating and recrystallizing the extract.

8. A method of treating a tumor or AIDS comprising the step of administering a compound of claim 1 into a subject.

9. A pharmaceutical composition comprising a pharmaceutically effective amount of a compound of claim 1 and pharmaceutically acceptable carrier.

10. A method of treating a tumor or AIDS comprising the step of administering the composition of claim 9 into a subject.

11. A intramolecular cyclizated compound having the formula (II) or (III)

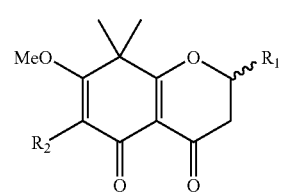

(II)

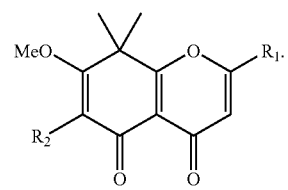

(III)

with the biological activity to tumor, AIDS, and viruses, produced by the intramolecular cyclization between $R_1$ and position 2-carbonyl in the compound of formula (I)

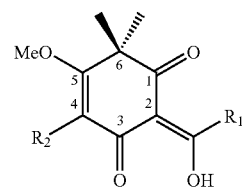

I wherein $R_1=C_2C_8R_1'$, $R_2$ is hydrogen, lower saturated or unsaturated alkyl, halogen, hydroxyl, alkoxyl, aryl, substituted aryl or heterocycle, provided that $R_2$ is not

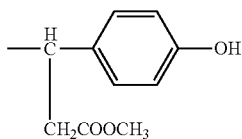

wherein $C_2$-$C_8$ is saturated or unsaturated alkyl that represents cis- and trans-isomer,
wherein $R_1'$ is selected from the groups consisting of aromatic ring; substituted aromatic ring with the group selecting from halogen, hydroxyl, lower alkyl, alkoxyl, furyl, thienyl, and thiazolyl; unsaturated aromatic heterocyclic ring; and substituted aromatic heterocyclic ring with the group selecting from halogen, hydroxyl, lower alkyl, alkoxyl, furyl, thienyl, and thiazolyl,
wherein $R_1$ is not styryl, isobutene, 1,2-dimethyl-1-propenyl, 1,2-dimethyl-phenylethane, 1,2-dibromo-phenethyl, and 2-hydroxy-styryl.

12. A compound of claim 11, wherein $R_1$ is —$CH_2$=$CH_2R1'$, $R_1'$ is selected from the group consisting of aromatic ring; aromatic ring substituted with the group selecting from halogen, hydroxyl, lower alkyl, alkoxyl, furyl, thienyl, and thiazolyl; unsaturated aromatic heterocyclic ring; and substituted aromatic heterocyclic ring with the group selecting from halogen, hydroxyl, lower alkyl, alkoxyl, furyl, thienyl and thiazolyl; $R_2$ is hydrogen, lower saturated or unsaturated alkyl, halogen, hydroxyl, alkoxyl, aryl, substituted aryl or heterocycle,
wherein $R_1$ is not styryl, isobutene, 1,2-dimethyl -1-propenyl, 1,2-dimethyl-phenylethane, 1,2-dibromo-phenethyl, and 2-hydroxy-styryl.

13. A compounds of claim 11, wherein $R_1'$ is selected from the groups consisting of 4-bromophenyl, 4-chlorophenyl, 4-iodophenylfluorone, hydroxy substituted phenyl, lower alkyl substituted phenyl, alkoxy substituted phenyl 2-furyl 2-thiophene and 2-thiazolyl; $R_2$ is hydrogen, lower saturated or unsaturated alkyl, halogen, hydroxyl, alkoxyl, aryl, substituted aryl or heterocycle.

14. A compounds of claim 11 selected from the group consisting of:
7-methoxy-6,8,8-trimethyl-2-phenyl-8H-chromene-4,5-dione, 7-methoxy-8,8-dimethyl-2-phenyl-8H-chromene-4,5-dione.

15. A method for preparing an intramolecular cyclizated compound of claim 11 having formula (II) or (III) comprising the steps of:
a) Conducting Improved Marchand reaction using 2,4,6-trihydroxyacctophenone as the initial material; dissolving 2,4,6,-trihydroxyacctophenone in AcOH, refluxing the 2,4,6,-trihydroxyacctophenone in AcOH in the presence of $Ac_2O$ and $BF_3OEt_2$; cooling and adjusted the mixture to pH2-6 by NaOH, extracting the mixture by 5% MeOH/AcOEt to obtain organic layers, combining the organic layers, following by drying and dissolving the organic layers in the MeOH to obtain a product; stirring the product with NaOH at room temperature; acidifying the product with HCL, then extracting the product with MeO/AcOEt to obtain an extract, washing, drying and purifying the extract by silica gel column to obtain 1,5-diacetyl -2,4,6-trihydroxybenzene;

b) Conducting a strong redox of 1,5-diacetyl -2,4,6-trihydroxybenzene with concentrated $H_2SO_4$ to obtain a mixture, methoxylating the mixture using $TMSCHN_2$, then extracting and isolating the mixture with MeOH/AcOEt to obtain 2-acetyl-5-methoxy-6,6-dimethylcyclohexane -1,3-dione;

c) Reacting a solution of 2-acetyl-5-methoxy-6,6-dimethylcyclohexane-1,3-dione in EtOH aq KOH with benzaldehyde in the presence of strong base to obtain a mixture; extracting the mixture by dichloromethane, then washing the mixture by water, following by drying, concentrating, isolating and recrystallizing the mixture to obtain 2-[(1' -hydroxyl-2'-ene-3'-phenyl)propenylene]-5-methoxy-6,6-dimethyl-1,3-cyclohexene(4,5)-dione;

d) Dissolving 2-[(1'-hydroxyl-2'-ene-3'-phenyl)propenylene]-5-methoxy-6,6-dimethyl-1,3-cyclohexene(4, 5)-dione in DMSO, and adding 0.5 v/w % $I_2$ and concentrated $H_2SO_4$ to obtain a mixture; heating the mixture; droplet adding the concentrated $H_2SO_4$ to the mixture; following by quenching the mixture in ice-cold bath with 10% $Na_2S_2O_3$; extracting the mixture with EtoAc to obtain an extract, washing the extract by water, following by drying, chromatographing the extract on silica gel to obtain the compound.

16. A method for preparing the intramolecular cyclizated compounds of claim 11 having formula (II) or (III) comprising the steps of:
a) Dissolving 2,4,6,-trihydroxyacctophenone in absolute alcohol, refluxing 2,4,6,-trihydroxyacctophenone in absolute alcohol with methyl iodide to obtain a mixture; cooling and acidifying the mixture with HCL, then extracting the mixture with EtOAc to obtain organic layers; combining the organic layers, drying and concentrating the organic layers to produce 2-acetyl -4,6,6-trimethylcyclonhexa-1,3,5-trione;

b) Selectively methoxylating 2-acetyl -4,6,6-trimethylcyclonhexa-1,3,5-trione to obtain 2-acetyl -3-hydroxy-5-methoxy-4,6,6- trimethylcyclonhexa-1,3-dione with −78° C. of the reaction temperature;

c) Stirring a solution of 2-acetyl -5-methoxy-4,6,6-trimethylcyclonhexa-1,3-dione in EtOH and 50% KOH in water and benzaldehyde at room temperature to obtain a mixture; extracting the mixture to obtain an extract, washing the extract with water, drying, concentrating, isolating and recrystallizing the extract to obtain 2-[(1'-hydroxy-2'-ene-3'-phenyl)propenylene]-5-methoxy-4,6,6-trimethyl -1,3-cyclohexene(4,5)-dione;

d) To a solution of 2-[(1'-hydroxy-2'-ene-3'-phenyl)propenylene]-5-methoxy-4,6,6-trimethyl -1,3-cyclohexene (4,5)-dione in DMSO, $I_2$ and concentrated $H_2SO_4$ is added to obtain a mixture; heating the mixture at 50~90° C., preferably 80° C.;
extracting the mixture and than washing, drying, and concentrating the mixture in vacuum.

17. A method of treating a tumor or AIDS comprising the step of administering a compound of claim 11 having formula (II) and/or (III) into a subject.

18. A pharmaceutical composition comprising a pharmaceutically effective amount of a compound of claim 11 having the formula (II) and/or (III) and pharmaceutically acceptable carrier wherein

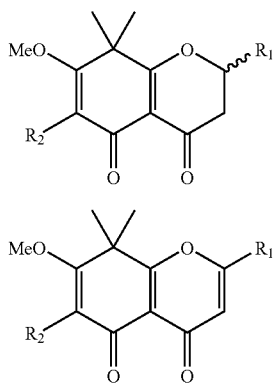

II

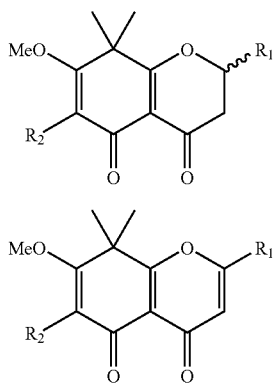

III wherein
$R_1 = C_2-C_8R_1'$,
$R_2$ is hydrogen, lower saturated or unsaturated alkyl, halogen, hydroxyl, alkoxyl, aryl, substituted aryl or heterocycle,
provided that $R_2$ is not

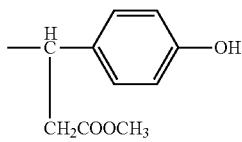

wherein $C_2-C_8$ is saturated or unsaturated alkyl that represents cis- and trans-isomer,
wherein $R_1'$ is selected from the groups consisting of aromatic ring; substituted aromatic ring with the group selecting from halogen, hydroxyl, lower alkyl, alkoxyl, furyl, thienyl, and thiazolyl; unsaturated aromatic heterocyclic ring; and substituted aromatic heterocyclic ring with the group selecting from halogen, hydroxyl, lower alkyl, alkoxyl, furyl, thienyl, and thiazolyl, wherein $R_1$ is not styryl, isobutene, 1,2-dimethyl-1-propenyl, 1,2-dimethyl-phenylethane, 1,2-dibromo-phenethyl, and 2-hydroxy-styryl.

19. A method of treating a tumor or AIDS comprising the step of administering the composition of claim 18 into a subject.

20. A method for preparing Desmosdumotin C having the following structure, comprising the steps of:

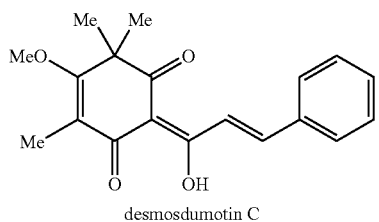

desmosdumotin C a) Dissolving 2,4,6,-trihydroxyacctophenone and sodium methoxide in absolute alcohol, refluenced in the presence of methyl iodide to obtain a mixture; cooling and acidifying the mixture with HCL, then extracting the mixture with EtOAc to obtain organic layers; combining the organic layers, drying and concentrating the organic layers to produce 2-Acetyl-4,6,6-trimethylcyclonhexa-1,3,5-trione;

b) Selectively methoxylating 2-Acetyl-4,6,6-trimethylcyclonhexa-1,3,5-trione to obtain 2-Acetyl-5-methoxy-4,6,6-trimethylcyclonhexa-1,3-dione with −78° C. of the reaction temperature;

c) Stirring a solution of 2-Acetyl-5-methoxy-4,6,6-trimethylcyclonhexa-1,3-dione in EtOH and 50% KOH in water and benzaldehyde at room temperature to obtain a mixture; extracting the mixture, washing the mixture with water, following by drying, concentrating, isolating and recrystallizing the mixture to obtain 2-[(1'-hydroxy-2'-ene-3'-phenyl)propenylene]-5-methoxy-4,6,6-trimethyl-1,3-cyclohexene(4,5)-dione.

* * * * *